US006392123B1

(12) United States Patent
Harper et al.

(10) Patent No.: US 6,392,123 B1
(45) Date of Patent: May 21, 2002

(54) FEMALE-PREFERENTIAL PROMOTERS ISOLATED FROM MAIZE AND WHEAT

(75) Inventors: Stacy Marie Harper, Chapel Hill, NC (US); Lyle Dean Crossland, Chesterfield, MO (US); Erica Pascal, Pittsboro, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/575,602

(22) Filed: May 22, 2000

Related U.S. Application Data

(62) Division of application No. 09/032,086, filed on Feb. 27, 1998.
(60) Provisional application No. 60/039,527, filed on Mar. 3, 1997.

(51) Int. Cl.$^7$ .................. C12N 15/29; C12N 15/82; A01H 5/00; A01H 5/10
(52) U.S. Cl. .............. 800/287; 536/23.6; 536/24.1; 500/278; 500/288
(58) Field of Search .................. 536/23.6, 24.1; 800/287, 278, 288

(56) References Cited

U.S. PATENT DOCUMENTS

| | | |
|---|---|---|
| 5,254,801 A | 10/1993 | Dotson et al. |
| 5,470,359 A | 11/1995 | Huffman |
| 5,633,441 A | 5/1997 | DeGreef et al. |
| 5,668,297 A | 9/1997 | Broer et al. |
| 5,767,370 A | 6/1998 | Broer et al. |
| 5,767,371 A | 6/1998 | Broer et al. |

FOREIGN PATENT DOCUMENTS

| | | |
|---|---|---|
| DE | 4129414 A1 | 3/1993 |
| EP | 0334383 A3 | 3/1989 |
| EP | 0412006 A1 | 7/1990 |
| EP | 0412911 A1 | 8/1990 |
| EP | 0436467 A2 | 12/1990 |
| WO | 90/08828 | 8/1990 |
| WO | 92/04454 | 3/1992 |
| WO | 94/25613 | 11/1994 |
| WO | 98/13504 | 4/1998 |
| WO | 98/39462 | 9/1998 |

OTHER PUBLICATIONS

Araya et al. pp. 83–91 In: Plant Mitochondria, Brennicke et al, eds, VCH: Weinheim, Germany, 1993.*

Mol. Biol. of the Cell, pp. 551–612, Garland Publishing, Inc.: New York, 1989.*

Cheung et al, A Floral Transmitting Tissue–Specific Glycoprotein Attracts Pollen Tubes and Stimulates Their Growth, Cell, vol. 82:383–393 Aug. 11, 1995.

Dotson et al, A phosphonate monoester hydrolase from Burkholderia caryophilli PG2982 is useful as a conditional lethal gene in plants, The Plant Journal (1996) 10(2), 383–392.

Dzelzkalns et al, Distinct cis–Acting Elements Direct Pistil–Specific and Pollen Specific Activity of the Brassica S Locus Glycoprotein Gene Promoter, The Plant Cell, vol. 5:855–863 Aug. 1993.

Goldman et al, Female sterile tobacco plants are produced by stigma–specific cell ablation, The EMBO Journal, vol. 13 No. 13: pp. 2976–2984, 1994.

Kandasamy et al, Ablation of Papillar Cell Function in Brassica Flowers Results in the Loss of Stigma Receptivity to Pollination, The Plant Cell, vol. 5:263–275 Mar. 1993.

Kriete et al, Male sterility in transgenic tobacco plants induced by tapetum–specific deacetylation of theexternally applied non–toxic compound N–acetyl–L–phosphinothricin, The Plant Journal, (1996) 9(6), 809–818.

Meinnel et al, Structural and Biochemical Characterization of the Escherichia coli argE Gene Product, Journal of Bacteriology, Apr. 1992, p. 2323–2331.

O'Keefe et al, Plant Expression of a Bacterial Cytochrome P450 That Catalyzes Activation of a Sulfonylurea Pro–Herbicide, Plant Physiol., 105; 473–482 (1994).

Savidge et al, Temporal Relationship between the Transcription of Two Arabidopsis MADS Box Genes and the Floral Organ Identity Genes, The Plant Cell, vol. 7:721–733 Jun. 1995.

Theissen et al, Structural characterization, chromosomal localization and phylogenetic evaluation of two pairs of AGAMOUS–like MADS–box genes from maize, Gene, 156 (1995) 155–166.

* cited by examiner

Primary Examiner—David T. Fox
(74) Attorney, Agent, or Firm—Erica Pascal; Edouard G. Lebel; J. Timothy Meigs

(57) ABSTRACT

The present invention provides a method for hybrid seed production comprising producing a conditional female sterile plant comprising a female-preferential promoter operably linked to a coding sequence which encodes an enzyme which catalyzes the conversion of a protoxin to a toxin, interplanting the conditional female sterile plant with a male sterile plant, applying the protoxin to the conditional female sterile plant, and producing hybrid seed. Viable seed formation is prevented on the conditional female sterile plant as a result of the conversion of the protoxin to the toxin in the female reproductive structures, and pollen production is prevented on the male sterile plant, thus allowing interplanting of the two parents of the hybrid cross in order to provide more efficient pollen transfer. Also provided are expression cassettes useful in the invention, plants transformed with the expression cassette, and novel female-preferential promoters.

42 Claims, 2 Drawing Sheets

FEMALE-PREFERENTIAL PROMOTERS ISOLATED FROM MAIZE AND WHEAT

This application is a divisional application of U.S. application Ser. No. 09/032,086, filed Feb. 27, 1998, which itself, claims the benefit of U.S. Provisional Application No. 160/039,527, filed Mar. 3, 1997.

FIELD OF THE INVENTION

The present invention relates to the production of hybrid seed in plants. In particular, the invention relates to a method of hybrid seed production using as one parent of the hybrid a plant transformed with a chimeric gene which when expressed in the female reproductive structures yields a protein that catalyzes the conversion of an exogenously-applied protoxin to a toxin, thereby rendering fertilization ineffective. Also included in the invention is the use of the conditional female-sterile plants in combination with conditional male-sterile plants to more efficiently produce hybrid seed, chimeric genes useful for the invention, transgenic plants comprising the chimeric genes, and novel promoters useful for expression in the female reproductive structures of a plant.

BACKGROUND OF THE INVENTION

Heterosis in crop plants has received considerable attention because of its marked effect on yield improvement. The increased productivity on crossing different strains of maize was first noted in the late 19th century and was then developed according to systematic genetic procedures. The usual method for raising hybrid maize is to establish many inbred lines, make intercrosses, and determine which hybrids are more productive in a given locality.

The success of hybrid maize motivated plant breeders to explore the existence and magnitude of hybrid vigor in many other species with economic importance. In general, hybrids exhibit increase yields in comparison to non-hybrid varieties. Hybrids are usually more efficient in use of growth factors and give a greater return per unit for the growth factors such as water and fertilizer. Under stress hybrids are generally superior to parental cultivars, with a more stable performance over a wide range of environments. With hybrids, there is uniformity in product and maturity that often facilitates harvest and increases the value of the product in the marketplace. The hybrid may also combine characters that are difficult or impossible to combine in other ways. This is particularly true of many interspecific and intergeneric hybrids. The general conclusion from research is that hybrid vigor, a common phenomenon in plants, is of sufficient magnitude to warrant commercial exploitation if appropriate techniques can be devised.

Hybrid vigor has been recognized as a wide-spread phenomenon in plants and animals for many years. Commercial hybrids are now used extensively in many crops, including maize, sorghum, sugar beet, and sunflower. Other large acreage crops such as wheat, barley and rice are still primarily grown as inbred varieties. Research is being conducted on these and other crops that may permit the wide-spread use of commercial hybrids in the future, but the primary limiting factor in new hybrid crop development is the lack of economical hybrid seed production methods in these crops.

Traditionally, large-scale hybrid seed production is accomplished by planting separate rows or blocks of female parent lines and the male parent lines to pollinate them. Only the seed produced on the female parent rows is harvested. To ensure that this seed is hybrid seed uncontaminated with selfed seed, pollination control methods must be implemented on the female parent plants to ensure that seeds formed on them result from cross-pollination and not self-pollination. Known pollination control mechanisms are generally mechanical, chemical, or genetic.

Elimination of fertile pollen from the female parent can be achieved by hand emasculation in some species such as maize, a monoecious species. Such elimination of fertile pollen is achieved by pulling or cutting the male inflorescence (tassel) from plants in the female parent population. This simple procedure prevents self-fertilization by mechanically detasseling female plants before pollen shed to prevent selfing. However, most major crop plants of interest have functional male and female organs within the same flower making emasculation impractical. Even where practical, this form of hybrid seed production is extremely labor intensive and hence expensive. To eliminate the laborious detasseling that is necessary to prevent self-fertilization in hybrid crosses, genetic factors which produce male-sterility have been used in some species.

Male-sterility in the female parent can be controlled by nuclear genes or by a cytoplasmic-genetic system. Genetic male-sterility is controlled by nuclear genes in which the alleles for sterility generally are recessive to the alleles for fertility. Genetic male-sterility occurs in many species. Usually, it is controlled by a single recessive gene that must be homozygous to cause male-sterility. Breeders who use genetic male-sterility for hybrid seed production usually develop a phenotypically uniform female line that segregates 50% male-sterile and 50% male-fertile individuals. Seed for these lines is increased in isolation by harvesting seed from plants homozygous for the male-sterility gene that are pollinated by plants heterozygous for the male-sterility gene, and hence male-fertile. To produce commercial hybrid seed with genetic male-sterility, the 50 percent of male-fertile female plants must be rogued from the field as soon as their fertility can be identified. The labor associated with roguing fertile plants from female plants has greatly restricted the use of genetic male-sterility in producing hybrid seed. There are several problems associated with this system for producing commercial hybrid seed. First, it is not possible to eliminate fertile plants from the desired male-sterile plants in the female population. Genetic male-sterile plants must be maintained by mating them with male-fertile individuals. Half of the $F_1$ plants from such a cross would be sterile, but the remaining plants would be fertile. Thus, the unwanted male-fertile plants in the female population may disseminate pollen and reduce the effectiveness of the desired male parent.

The successful use of cytoplasmic male-sterility for commercial hybrid seed production requires a stable male-sterile cytoplasm, an adequate pollen source, and an effective system of getting the pollen from the male parent to the male-sterile female. Also, the cytoplasmic-genetic system of male sterility requires three lines to produce a single crossed hybrid; the A line (male-sterile), B line (male-fertile maintainer), and R line (male-fertile with restorer genes). Three-way crosses produced with cytoplasmic-genetic male sterility involved maintenance and production of four lines, an A and B line of one inbred and male-fertile inbreds of the other two.

Furthermore, the southern maize blight caused by *Helminthosporium maydis,* Race T, which severely attacked all maize hybrids with cytoplasmic male-sterile T cytoplasm, demonstrated the vulnerability of a hybrid seed production industry based on a single source of male-sterile cytoplasm.

For hybrid maize, most seed producers have returned to hand or mechanical emasculation and wind pollination.

Hybrid seed may also be produced by the use of chemicals that block or kill viable pollen formation. These chemicals, called gametocides, are used to impart a transitory male-sterility. However, the expense and availability of the chemicals and the reliability of the applications limits the production of hybrid seed through the use of gametocides.

Molecular methods for hybrid seed production have also been described. Such methods transform plants with constructs containing anti-sense DNA and other genes which are capable of controlling the production of fertile pollen into plants. Such regenerated plants are functionally male-sterile and are used for the production of hybrid seed by crossing with pollen from male-fertile plants. The primary deficiencies of these approaches stem from the fact that the genetically engineered male sterility gene, whether it is an anti-sense or RNAse, can only be maintained in a heterozygous state. They are fundamentally the same as natural genetic male steriles in that they must be maintained by crossing to isogenic male fertile lines. This is most problematic in the hybrid cross field where the acreage is large and yield is critical. The heterozygous female parent, of which only 50% will be male sterile, must be planted in rows next to the pollen donor male parent and the 50% fertile female parents removed. This is rendered easier in genetically engineered genetic male steriles because a herbicide resistance gene can be linked to the male sterility gene, and herbicide spray can be used to remove the fertile plants, but it still means that the female parent rows must be planted at double density in order to get the same yield per acre of our system. This will cause some yield loss due to competition. The herbicide spray also means yield loss because the resistant plants are never 100% immune to the herbicide, and the costs of spraying the chemical are considerable.

A shortcoming of these traditional hybrid seed production systems is the need to plant separate rows or blocks of the male and female parent lines. The physical distance between the male pollen donor and female pollen recipient plants results in less efficient pollen transfer, poor seed set on the female parent, the need to dedicate more production land to pollen donor plants, and less yield of hybrid seed per unit area of land. This shortcoming is especially acute in crop species such as wheat that release small amounts of pollen, and the pollen is not effectively carried by the wind. Traditional hybrid seed production methods when applied to wheat have required from one third to two thirds of the production field be dedicated to male pollen donor plants (Johnson and Schmidt, Adv. Agronomy 20:199–233 (1968); Wilson, Plant Breeding Reviews 303–309 (1989)). The result is the cost of hybrid wheat seed production is too high to sustain an industry despite the availability of hybrid seed production techniques and proven heterosis.

To achieve a more economical hybrid seed production system for wheat and other crops, it is necessary to move the male and female parent plants closer together to effect more efficient pollen transfer. Rather than being in separate blocks of rows so that seed from only the female parent plants can be harvested, the male and female parent plants need to be interplanted in the same rows meaning that the plants are centimeters, rather than meters apart. Since it would be impractical to harvest seed from only the female parents when so closely spaced to make parents, it is necessary to prevent formation of viable seed on the male parent plants in addition to preventing formation of viable pollen on the female parent plants.

One method of preventing formation of viable seed is the use of female-sterile plants. Naturally occurring female sterility has been reported in several crops (Honma and Phatak, Journal of Heredity 55:143–145 (1964); Sniezdo and Winiarczyk, Protoplasma 187:31–38 (1995); Justus and Meyer, Journal of Heredity 54:167–168 (1963); Hanna and Powell, Journal of Heredity 65:247–249 (1974); Brown and Bingham, Crop Science 24:1207–1208 (1984)) but there are problems in maintaining these lines and they a,re not used commercially. A method for constructing a dominant, female-sterility gene has been described (EP 412,006 A1 (1990); Goldman et al., EMBO Journal 13:2976–2984 (1994)), but again the maintenance of a female-sterile line containing this gene is problematic due to the inability to create a line homozygous for the female-sterility gene. A method for maintenance and use in hybrid seed production of this female-sterility gene has been described (EP 402,270 (1990)). However, it requires the introduction of a female-sterility gene, a restorer gene of a first male-sterility gene, a second male-sterility gene and two herbicide resistance genes in a complex series of sequential transformations to create the female-sterile male parent line, and it requires the introduction of the first male-sterility gene, a restorer gene of the female-sterility gene and an herbicide resistance gene in a complex series of sequential transformations to create the male-sterile female parent line. Herbicide treatment is needed to select the correct genotypes at each round of line multiplication, and to produce the hybrid seed the production field needs to be treated with one of the herbicides to kill off undesirable genotypes that are a result of the process. Although the above system could provide the economic advantage of interplanting of the male and female lines, it is too complex for commercial utility.

Accordingly, there is a need for a simple, economical method for hybrid seed production.

SUMMARY OF THE INVENTION

The present invention provides a method for hybrid seed production comprising producing a conditional female sterile plant comprising a female-preferential promoter operably linked to a coding sequence which encodes an enzyme which catalyzes the conversion of a protoxin to a toxin, interplanting the conditional female sterile plant with a male sterile plant, inducing female sterility by applying the protoxin to the conditional female sterile plant, and producing hybrid seed. In one preferred embodiment of the invention, the plant is either normally self-pollinated or normally cross-pollinated. In particularly preferred embodiments, the plant is selected from the group consisting of maize, wheat, and barley. Also provided by the invention are hybrid seeds produced by the method.

The invention further provides an expression cassette comprising a female-preferential promoter operably linked to a coding sequence which encodes an enzyme which catalyzes the conversion of a protoxin to a toxin. A preferred embodiment comprises a female-preferential promoter operably linked to the coding sequence of the argE gene. Preferred embodiments of female-preferential promoters consist of the promoter from either the B200i4-2 clone, the P26 clone or the P19 clone. A particularly preferred embodiment comprises the female-preferential promoter from either the B200i4-2 clone or the P19 clone operably linked to the argE coding sequence. Additional embodiments of coding sequences useful in the invention are those obtained from the $P450_{sul}$ monoxygenase gene, and the pehA gene.

Also provided by the invention are plants comprising the expression cassette comprising a female-preferential promoter operably linked to a coding sequence which encodes an enzyme which catalyzes the conversion of a protoxin to a toxin, and seeds of such plants.

Another object of the invention is the use of a protoxin in a method of inducing female fertility in a plant which comprises a female-preferential promoter operably linked to a coding sequence which encodes an enzyme which catalyzes the conversion of a protoxin to a toxin, and inducing female sterility by applying the protoxin to the plant.

Yet another object of the invention is the use of the coding sequence from the argE gene in a method for producing for hybrid seed where the argE coding sequence is operably linked to a female-preferential promoter which when expressed catalyzes the conversion of a protoxin to a toxin thereby inducing female sterility.

DETAILED DESCRIPTION OF THE INVENTION

Definitions and Nomenclature

Figure 1:
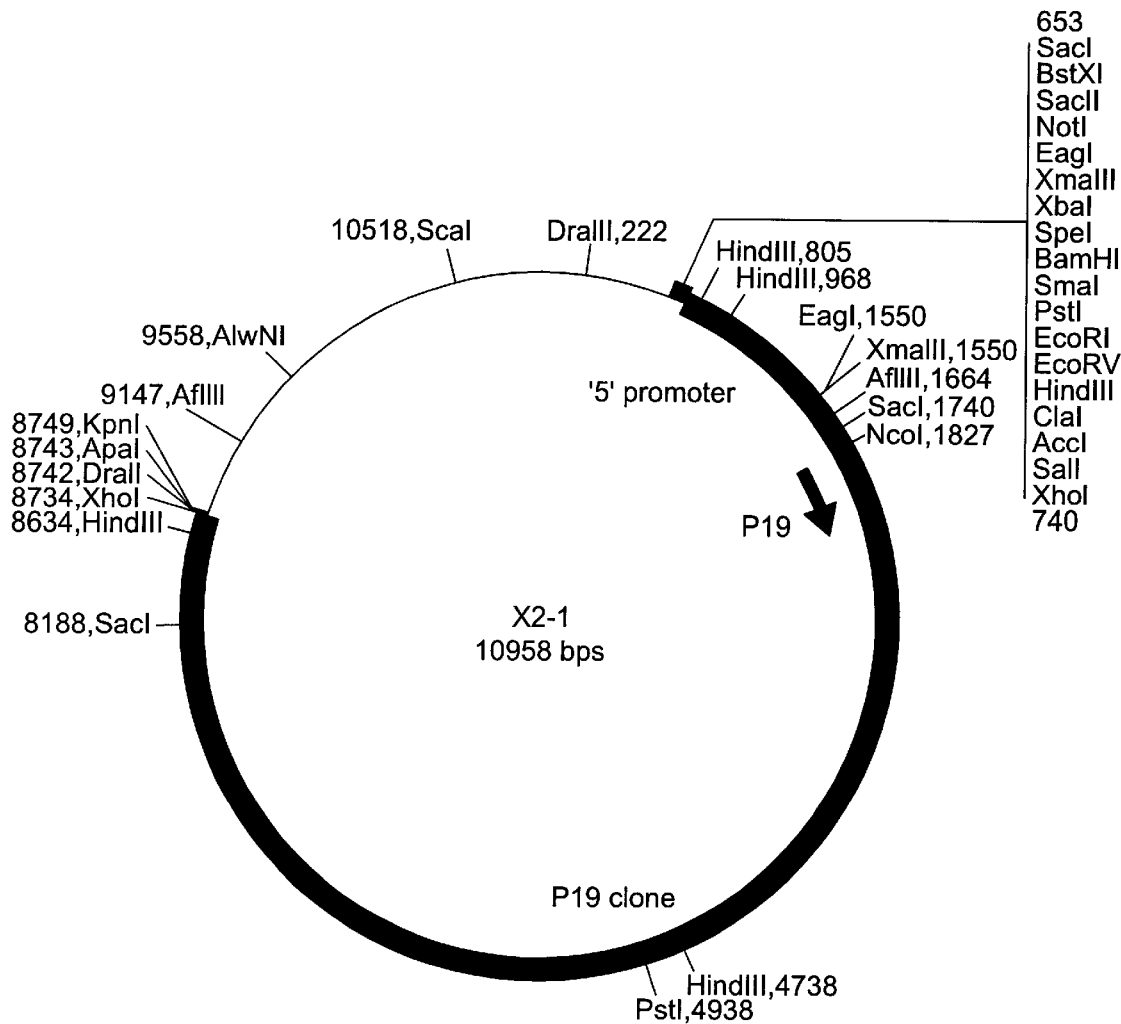
FIG. 1 shows plasmid X2-1.
Figure 2:
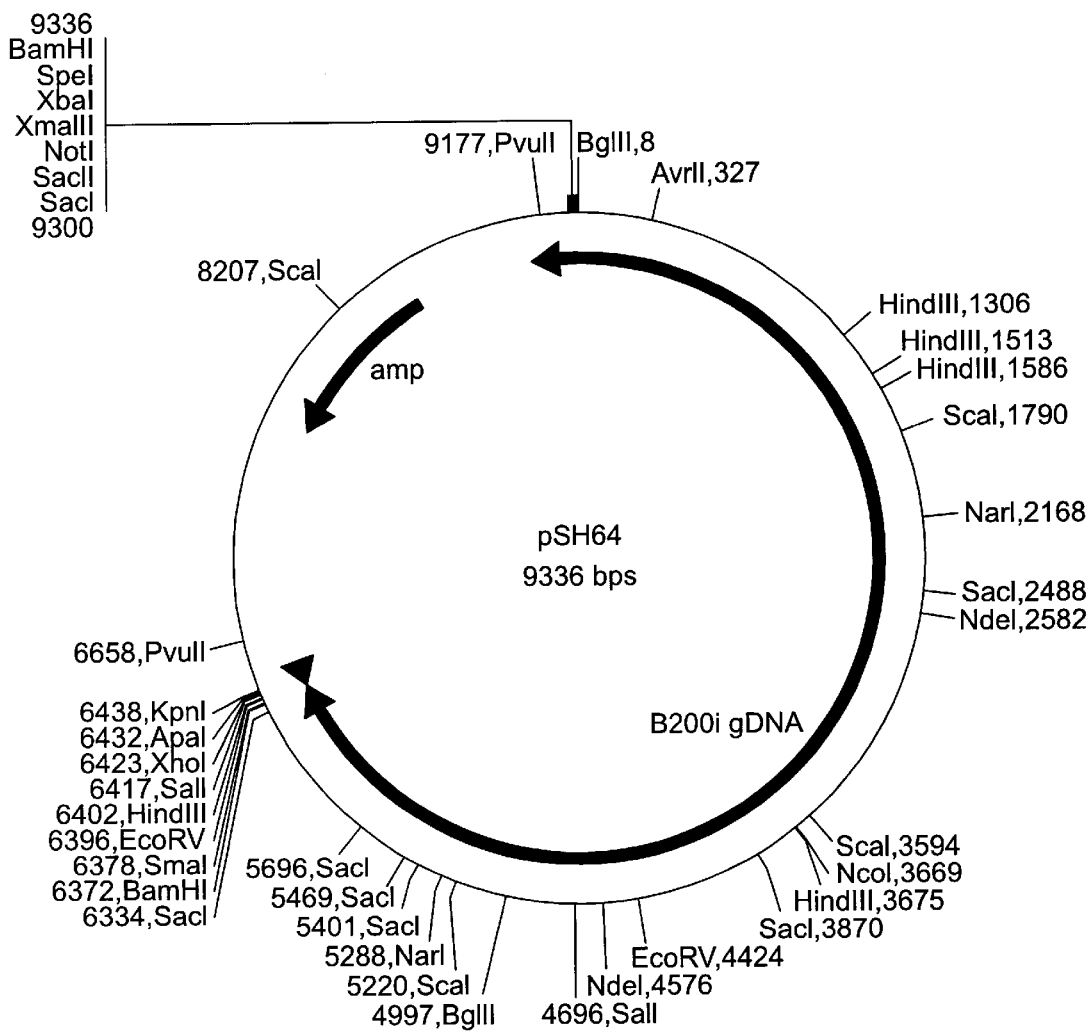
FIG. 2 shows plasmid pSH64.

The term "female reproductive structure" as used herein means those portions of a plant which compose the carpel, or gynoecium (an old established term used with regard to the gynoecium is "pistil"). The carpel of a flower of a plant includes but is not limited to a stigma, style, ovary, and cells or tissues which comprise the stigma, style and ovary, A "female-preferential" promoter as used herein means a promoter having transcriptional activity only in or primarily in one or more of the cells or tissues of a female reproductive structure of a plant.

"Expression cassette" as used herein means a DNA sequence capable of directing expression of a gene in plant cells, comprising a promoter operably linked to an amino acid coding region which is operably linked to a termination region. The gene may be chimeric, meaning that at least one component of the gene is heterologous with respect to at least one other component of the gene. The gene may also be naturally occuring, but which has been obtained in a recombinant form useful for genetic transformation of a plant.

"Protoxin" as used herein means a chemical with minimal phytotoxicity that can be activated by the action of an enzyme to produce a reaction product that is toxic to plant cells or disrupts plant cell functions in a manner sufficient to retard, suppress or prevent normal growth, development or metabolic activity. The toxic reaction product is referred to herein as a "toxin." In the invention, the protoxin is applied exogenously to the plant, which may be accomplished any means which facilitates foliar absorption, root absorption, direct contact with the targeted plant parts, or systemic movement from one part of the plant to another.

"Female fertility" as used herein means that the female reproductive structures of a plant are capable of supporting viable seed formation when pollinated with functional or viable pollen. "Female sterility" as used herein means that the female reproductive structures of a plant are not capable of supporting viable seed formation when pollinated with functional or viable pollen. "Conditional female sterility" as used herein means that female sterility is produced upon the exogenous application of a protoxin which is subsequently activated by an enzyme to produce a toxic reaction product. "Male sterility" as used herein means that the male reproductive structures of a plant are incapable of producing viable or functional pollen.

Control of Female Fertility in Plants

One of the advantageous aspects of the present invention is its use in the control of viable seed formation in plants under field conditions by controlling female fertility. Fertility of the female can be controlled by obtaining a transgenic plant comprising a chimeric or recombinant nucleotide sequence encoding an enzyme which catalyzes the conversion of a protoxin to a toxin, which when expressed under the control of a female-preferential promoter will render the female reproductive structures incapable of viable seed formation upon exogenous application of the protoxin. The transgenic plants are said to be conditional for female sterility because the appearance of female sterility is conditioned upon the presence of the protoxin. The conversion of a protoxin to a toxin in the female reproductive structures could prevent viable seed formation through several mechanisms, depending on when, and in what cells or tissues, the female-preferential promoter is active. These include but are not limited to: 1) disruption of normal pistil development such that the pistil is no longer competent to allow fertilization, 2) inhibition of pollen tube growth by the converted toxin, 3) disruption of the development of viable gametes, and 4) disruption of seed development following fertilization.

In one embodiment of the present invention, a protoxin is exogenously applied to transgenic plants under field conditions and conversion of the protoxin to the toxin occurs in the female reproductive structure. Viable seed formation is prevented by the action of the toxin in the female reproductive structure.

Coding Sequences and Protoxins Useful in the Invention

Useful coding sequences for the invention include but are not limited to any sequence which encodes a protein capable of converting a protoxin to a toxin. These coding sequences can be of either a homologous or heterologous origin.

In one preferred embodiment, the coding sequence from the argE gene is operably linked to a female-preferential promoter. Expression of this chimeric gene in a transgenic plant results in conditional female sterility in the presence of the protoxin N-acetyl phosphinothricin (N-acetyl PPT). The gene product of the argE gene is the N-acetyl-L-ornithine deacetylase of *E. coli*, which has a broad specificity for hydrolysis of substrates of the type $R_1$—CO—NH—CH$((CH_2)$—$R_2)$—COOH. As a result of this activity, the argE gene product catalyzes the conversion of the protoxin acetylphosphinothricin to the toxin phosphinothricin (PPT) (Kiete et al., *The Plant Journal* 9:809–818 (1996)).

In another preferred embodiment, the coding sequence from the gene for the $P450_{sul}$ monooxygenase, CPY105A1, is operably linked to a female-preferential promoter. This expression results in conditional female sterility in the presence of a sulfonamide protoxin. The *Streptomyces griseolus* $P450_{sul}$ monooxygenase, when targeted to the chloroplast, mediates the N-dealkylation of the sulfonyl urea compound R7402 (2-methylethyl-2,2-dihydro-N-[(4,6-dimethoxypyrimidin-2-yl)aminocarbonyl]-1,2-benzoiaothiazole-7-sulfonamide-1,1-dioxide and converts it to a toxin (O'Keefe et al. Plant Physiology 105:473–482 (1994)).

In yet another preferred embodiment, the coding sequence of the pehA gene is operably linked to a female-preferential promoter and this expression results in conditional female sterility in the presence of the protoxin, glyceryl glyphosate. The gene product of the *Burkholderia caryophili* PG2982 pehA gene is a phosphonate monoester hydrolase which catalyzes the conversion of the protoxin glyceryl glyphosate to the toxin glyphosate (Dotson et al., Plant Journal 10:383–392 (1996)).

The above examples are given by way of illustration and not limitation. Any coding sequence which encodes an enzyme which catalyzes the conversion of a protoxin to a toxin may be used in the invention, provided that it is operably linked to a female-preferential promoter.

Promoters Useful in the Invention

In order to practice the invention it is desirable that the above nucleotide sequences encoding an enzyme which catalyzes the conversion of a protoxin to a toxin be operably linked to a 5' regulatory sequence which directs its expression in a manner which is preferential to the female reproductive structures of a plant. This specificity in expression ensures that the effect of the expressed enzyme will be exerted only on those tissues or cells which are necessary for the formation of viable seeds and will not be deleterious to the plant beyond its affect on fertility.

Female-preferential promoters useful in the present invention in plants include but are not limited to, dicot promoters such as a modified S13 promoter (Dzelkalns et al., *Plant Cell* 5:855 (1993)), the Stig1 promoter of tobacco (Goldman et al., *EMBO J.* 13:2976–2984 (1994)), the AGL5 promoter (Savidge et al., Plant Cell 7:721–733 (1995)), and the promoter from tobacco TTS1 (Cheung et al., Cell 82:383–393 (1995)). The above promoters have all been tested and shown to be functional in transgenic plants. Monocot derived promoters include the promoter of the maize carpel-specific ZAG2 gene (Thiessen et al., Gene 156:155–166 (1995)).

Additionally, genomic DNA containing promoter sequences can be isolated which correspond to a cDNA known in the art to have female preferential expression. These include, but are not limited to, promoters for the Arabidopsis Fbp7 and Fbp11 genes (Angenent et al., Plant Cell 7:1569–1582 (1995)) and the orchid female-specific cDNAs O40, O108, O39, O126 and O141 (Nadeau et al., Plant Cell 8:213–239 (1996)).

Female-preferential genes useful for specific plant species can be cloned by isolating novel transcripts expressed in female tissues using techniques known to those skilled in the art. This involves isolating RNA from female tissues such as maize silk or wheat pistils, and differentially screening by techniques such as differential display, PCR select cDNA subtraction and subtractive cDNA library construction to isolate cDNA clones that are preferentially expressed in the female tissues and not in other parts of the plant such as leaf, root or tassel. The tissue specificity of these cloned cDNAs can be confirmed by Northern analysis. The promoter sequences for female preferential clones can then be obtained by using the isolated novel cDNAs as probes for genomic library screening. Genomic clones can be isolated which contain 5' and 3' regulatory sequences needed for expression in female tissue. These sequences can be used to construct expression cassettes for expression of chimeric genes in a female-preferential manner.

Other Regulatory Elements Useful in the Invention

The 5' regulatory region of the expression cassette may also include other enhancing sequences. Numerous sequences have been found to enhance gene expression in transgenic plants. For example, a number of non-translated leader sequences derived from viruses are known to enhance expression. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15:8693–8711 (1987); Skuzeski et al. *Plant Molec. Biol.* 15:65–79 (1990)). Other leaders known in the art include but are not limited to:

Picornavirus leaders, for example, EMCV leader (Encephalomyocarditis 5' noncoding region) (Elroy-Stein, O., Fuerst, T. R., and Moss, B. *PNAS USA* 86:6126–6130 (1989));

Potyvirus leaders, for example, TEV leader (Tobacco Etch Virus) (Allison et al., (1986); MDMV leader (Maize Dwarf Mosaic Virus); *Virology*, 154:9–20);

Human immunoglobulin heavy-chain binding protein (BiP) leader, (Macejak, D. G., and Sarnow, P., *Nature*, 353: 90–94 (1991);

Untranslated leader from the coat protein mRNA of alfalfa mosaic virus (AMV RNA 4), (Jobling, S. A., and Gehrke, L., *Nature*, 325:622–625 (1987);

Tobacco mosaic virus leader (TMV), (Gallie, D. R. et al., *Molecular Biology of RNA*, pages 237–256 (1989); and Maize Chlorotic Mottle Virus leader (MCMV) (Lommel, S. A. et al., *Virology*, 81:382–385 (1991). See also, Della-Cioppa et al., *Plant Physiology*, 84:965–968 (1987).

Various intron sequences have been shown to enhance expression when added to the 5' regulatory region, particularly in monocotyledonous cells. For example, the introns of the maize Adh1 gene have been found to significantly enhance the expression of the wild-type gene under its cognate promoter when introduced into maize cells (Callis et al., *Genes Develop.* 1:1183–1200(1987)).

In addition to promoters, a variety of 3'transcriptional terminators are also available for use in the present invention. Transcriptional terminators are responsible for the termination of transcription and correct mRNA polyadenylation. Appropriate transcriptional terminators and those which are known to function in plants include the CaMV 35S terminator, the tml terminator, the nopaline synthase terminator, the pea rbcS E9 terminator and others known in the art. These can be used in both monocotyledons and dicotyledons.

Plant Transformation

The expression cassettes of the present invention can be introduced into the plant cell in a number of art-recognized ways. Those skilled in the art will appreciate that the choice of method might depend on the type of plant, i.e. monocotyledonous or dicotyledonous, targeted for transformation. Suitable methods of transforming plant cells include, but are not limited to, microinjection (Crossway et al., *BioTechniques* 4:320–334 (1986)), electroporation (Riggs et al., *Proc. Natl. Acad. Sci. USA* 83:5602–5606 (1986), Agrobacterium-mediated transformation (Hinchee et al., *Biotechnology* 6:915–921 (1988)), direct gene transfer (Paszkowski et al., *EMBO J.* 3:2717–2722 (1984)), and ballistic particle acceleration using devices available from Agracetus, Inc., Madison, Wis. and BioRad, Hercules, Calif. (see, for example, Sanford et al., U.S. Pat. No. 4,945,050; and McCabe et al., *Biotechnology* 6:923–926 (1988)). Also see, Weissinger et al.,*Annual Rev. Genet.* 22:421477 (1988); Sanford et al., *Particulate Science and Technology* 5:27–37 (1987)(onion); Christou et al., *Plant Physiol.* 87:671–674 (1988)(soybean); McCabe et al., *Bio/Technology* 6:923–926 (1988)(soybean); Datta et al., *Bio/Technology* 8:736–740 (1990)(rice); Klein et al., *Proc. Natl. Acad. Sci. USA*, 85:4305–4309 (1988)(maize); Klein et al., *Bio/Technology* 6:559–563 (1988)(maize); Klein et al., *Plant Physiol.* 91:440–444 (1988)(maize); Fromm et al., *Bio/Technology* 8:833–839 (1990)(maize); and Gordon-Kamm et al., *Plant Cell* 2:603–618 (1990)(maize); Svab et al., *Proc. Natl. Acad. Sci. USA* 87: 8526–8530 (1990)(tobacco chloroplast); Koziel et al., *Biotechnology* 11: 194–200 (1993)(maize); Shimamoto et al., *Nature* 338: 274–277 (1989)(rice); Christou et al., *Biotechnology* 9: 957–962 (1991)(rice); European Patent Application EP 0 332 581, Horn et al. (orchardgrass and other Pooideae); Vasil et al., *Biotechnology* 11: 1553–1558 (1993)(wheat); Weeks et al., *Plant Physiol.* 102: 1077–1084 (1993)(wheat); Wan and Lemaux, *Plant Physiol.* 104, 37–48 (1994)(barley).

One particularly preferred set of embodiments for the introduction of the expression cassettes of the present invention into maize by microprojectile bombardment is described in U. S. Ser. No. 08/008,374, herein incorporated by reference in its entirety. An additional preferred embodiment is the protoplast transformation method for maize as disclosed in European Patent Application EP 0 292 435, as well as in U.S. Pat. No. 5,350,689, hereby incorporated by reference in its entirety. One particularly preferred set of embodiments for the introduction of the expression cassettes of the present invention into wheat by microprojectile bombardment can be found in U.S. Pat. No. 5,610,042 herein incorporated by reference in its entirety.

Transformation of plants can be undertaken with a single DNA molecule or multiple DNA molecules (i.e. co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

Many vectors are available for transformation using *Agrobacterium tumefaciens*. These typically carry at least one T-DNA border sequence and include vectors such as pBIN19 (Bevan, *Nucl. Acids Res. (*1984)). In one preferred embodiment, the expression cassettes of the present invention may be inserted into either of the binary vectors pCIB200 and pCIB2001 for use with Agrobacterium. These vector cassettes for Agrobacterium-mediated transformation were constructed in the following manner. pTJS75kan was created by NarI digestion of pTJS75 (Schmidhauser & Helinski, *J Bacteriol.* 164: 446–455 (1985)) allowing excision of the tetracycline-resistance gene, followed by insertion of an AccI fragment from pUC4K carrying an NPTII (Messing & Vierra, *Gene* 19: 259–268 (1982); Bevan et al., *Nature* 304: 184–187 (1983); McBride et al., *Plant Molecular Biology* 14: 266–276 (1990)). XhoI linkers were ligated to the EcoRV fragment of pCIB7 which contains the left and right T-DNA borders, a plant selectable nos/nptII chimeric gene and the pUC polylinker (Rothstein et al., *Gene* 53: 153–161 (1987)), and the XhoI-digested fragment was cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. The plasmid pCIB2001 is a derivative of pCIB200 which was created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI pCIB2001, in addition to containing these unique restriction sites also has plant and bacterial kanamycin selection, left and right T-DNA borders for Agrobacterium-mediated transformation, the RK2-derived trFA function for mobilization between *E. coli* and other hosts, and the OriT and OriV functions also from RK2. The pCIB2001 polylinker is suitable for the cloning of plant expression cassettes containing their own regulatory signals.

An additional vector useful for Agrobacterium-mediated transformation is the binary vector pCIB10, which contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al., *Gene* 53: 153–161 (1987). Various derivatives of pCIB10 have been constructed which incorporate the gene for hygromycin B phosphotransferase described by Gritz et al., *Gene* 25: 179–188 (1983). These derivatives enable selection of transgenic plant cells on hygromycin only (pCIB743), or hygromycin and kanamycin (pCIB715, pCIB717).

Methods using either a form of direct gene transfer or Agrobacterium-mediated transfer usually, but not necessarily, are undertaken with a selectable marker which may provide resistance to an antibiotic (e.g., kanamycin, hygromycin or methotrexate) or a herbicide (e.g., phosphinothricin). The choice of selectable marker for plant transformation is not, however, critical to the invention unless the expression of this resistance and its biochemical activity interferes with the choice of protoxin to toxin conversion chosen for use in creating conditional fertility.

For certain plant species, different antibiotic or herbicide selection markers may be preferred. Selection markers used routinely in transformation include the nptII gene which confers resistance to kanamycin and related antibiotics (Messing & Vierra, *Gene* 19: 259–268 (1982); Bevan et al., *Nature* 304:184–187 (1983)), the bar gene which confers resistance to the herbicide phosphinothricin (White et al., *Nucl Acids Res* 18:1062 (1990), Spencer et al., *Theor Appl Genet* 79:625–631(1990)), the hph gene which confers resistance to the antibiotic hygromycin (Blochinger & Diggelmann, *Mol Cell Biol* 4: 2929–2931), the dhfr gene, which confers resistance to methotrexate (Bourouis et al., *EMBO J.* 2: 1099–1104 (1983)), the mannose phosphate isomerase gene, which allows selection on mannose as a carbon source (EP 530 129,WO 94/20627).

One such vector useful for direct gene transfer techniques in combination with selection by the herbicide Basta (or phosphinothricin) is pCIB3064. This vector is based on the plasmid pCIB246, which comprises the CaMV 35S promoter in operational fusion to the *E. coli* GUS gene and the CaMV 35S transcriptional terminator and is described in the PCT published application WO 93/07278, herein incorporated by reference. One gene useful for conferring resistance to phosphinothricin is the bar gene from *Streptomyces hygroscopicus* (Thompson et al., *EMBO J* 6: 2519–2523 (1987)). This vector is suitable for the cloning of plant expression cassettes containing their own regulatory signals. It should be noted, however, that the use of bar as a selectable marker can interfere with the operation of the present invention if it is also expressible in female reproductive structures. This problem can be overcome by the use of promoters which control expression in the cell or tissue cultures used for transformation, but do not result in bar gene expression in the female reproductive structures.

Another transformation vector is the vector pGL2 (Shimamoto et al. *Nature* 338, 274–276 (1989) which contains the Streptomyces hygromycin phosphotransferase gene (hpt) operably linked to the 35S promoter and 35S terminator sequences.

An additional transformation vector is pSOG35 which utilizes the E. coli gene dihydrofolate reductase (DHFR) as a selectable marker conferring resistance to methotrexate. PCR was used to amplify the 35S promoter (~800 bp), intron 6 from the maize Adh1 gene (~550 bp) and 18 bp of the GUS untranslated leader sequence from pSOG10. A 250 bp fragment encoding the E. coli dihydrofolate reductase type II gene was also amplified by PCR and these two PCR fragments were assembled with a SacI-PstI fragment from pBI221 (Clonetech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC-derived gene for ampicillin resistance and have HindIII, SphI, PstI and EcoRI sites available for the cloning of foreign sequences.

Producing Hybrid Seed Using Conditional Female Sterility

In order to produce hybrid seed uncontaminated with seed produced by self-pollination, pollination control methods must be implemented to prevent self-pollination of the female parent and ensure cross-pollination by the male parent. This is usually accomplished by mechanical methods, genetic male-sterility or chemical hybridizing agents (CHAs). For example, in maize the current practice is mechanical detasseling of the female (or seed) parent, which is a time consuming and labor intensive process. In wheat, controlling fertility by mechanical means is impractical on a seed production scale, and genetic sources of male-sterility are not commercially established. Methods of hybrid seed production based only on pollination control require that blocks of male parent plants be physically separate from blocks of female parent plants, as the male parent plants will produce seed from self-pollination. The use of the present invention in the production of hybrid seed offers the advantages of reliability, ease of use and most importantly will allow interplanting of male and female parent plants, resulting in more efficient pollen transfer, the need for fewer male parent plants, and more economical hybrid seed production.

In order to produce hybrid seed using the invention, a transgenic parent plant which expresses a enzyme which catalyzes the conversion of a protoxin to a toxin in a female-preferential manner is required. Obtaining transgenic plants possessing this genotype are described above. The transgenic plants containing the chimeric or recombinant genes of the present invention can be made homozygous and maintained indefinitely using normal plant breeding methodologies.

Also required for the production of hybrid seed according to the invention is a parent plant which is male sterile. Male sterility is the failure or inability to produce viable or functional pollen. Male sterility may result from disruptions leading to the non-formation of pollen or to the lack of functional ability in the pollen when it is formed. Therefore, either pollen is not formed or, if formed, it is either non-viable or incapable of effective fertilization under normal conditions.

Many sources of male sterility for use in hybrid seed production are known (Kaul, Male Sterility in Higher Plants, Springer-Verlag (1988)). Naturally occurring cytoplasmic male sterility genes and their use have been described for maize (Levings, Science 250:942–947 (1990), wheat (Toriyama et al., Jpn. J. Breed. 43:517–524 (1993)), tobacco (Gerstel et al., Genetics 89:157–169 (1978)), rye (Steinborn et al., Theor. Appl. Genet. 85:822–824 (1993)), sunflower (Crouzillat et al., Plant Mol. Biol. 16:415–426 (1991)), soybean (Davis, U.S. Pat. No. 4,763,441 (1988)), Brassica (Grelon et al., Mol. Gen. Genet. 243:540–547 (1994)), carrot (Kitagawa et al., Sex. Plant Reprod. 7:41–50 (1994)), sorghum (Chen et al., Plant Mol. Biol. 28:799–809 (1995)), rice (Kadowaki et al., Mol. Gen. Genet. 224:10–16 (1990)) and barley (Kaul and Singh, Cytobios 66:71–85 (1991)).

The construction of chimeric or recombinant male sterility genes is also known. A gene encoding a β-1,3-glucanase, when expressed from a promoter active only in the tapetal cells of the anther, has been shown to cause male sterility in transgenic plants (Worrall et al., Plant Cell 4:759–771 (1992)). A gene encoding an unedited atp9 mitochondrial gene from wheat has been shown to cause male sterility when expressed from the constitutive CaMV 35S promoter in transgenic plants (Hernould et al., Proc. Natl. Acad. Sci. USA 90:2370–2374 (1993)). A gene encoding an RNAse enzyme has been shown to cause male sterility when expressed from a promoter active only in the tapetal cells of the anther in transgenic plants (DeBlock et al., Planta 189:218–225 (1993); EP 344,029; Mariani et al., Nature 347:737–741 (1990)). Expression of an antisense RNA complementary to a gene critical to pollen formation has been shown to cause male sterility in transgenic plants (EP 513,884).

Additionally there are many other male-specific promoters that are well known in the art and could be utilized in the construction of chimeric male-sterility genes. These include promoter sequences for expression in pollen, the tapetum or other structures in the anther. Examples of male specific promoters include but are not limited to the LAT52 promoter (Twell et al., Dev. 109:705–13 (1989)), the tomato A127 promoter (Dotson et al. Plant J. 10, 383–392. (1996)), the maize Zmg promoter (Hamilton et al. Sex. Plant Reprod. 2:208–212 (1989)), the maize CDPK promoter (Guerro et al., Mol. Gen Genet. 224:161–168 (1990)), the anther-specific ant32 and ant43D promoters disclosed in U.S. Pat. No. 5,477,002, herein incorporated by reference in its entirety. Additionally, promoter sequences for anther-specific cDNAs can be cloned by isolating the corresponding genomic DNA sequences and defining the promoter regulatory regions, for example, isolating promoter sequences for the orchid pollen tube-specific P450 (Nadeau et al., Plant Cell 8:213–239 (1996)) and the Bcp1 of Arabidopsis (Xu et al. Proc. Natl Acad. Sci. 92:2106–2110 (1995)). Similarly, novel genes that are male-specific can be isolated by a variety of techniques such as differential display, PCR select cDNA subtraction and differential cDNA library screening. Once identified, corresponding genomic sequences can be isolated, the promoter regions characterized, and these sequences are then used as promoter regions to construct expression cassettes expressed in a male-specific manner.

The above artificial male sterility genes have the disadvantage that their action is unconditional and dominant. Once the transgenic plant is created it is always male sterile, making maintenance of plant lines difficult and making it impossible to create a homozygous, true breeding plant line.

Another category of male sterility genes have been described in which the male sterile phenotype is conditional. In this category, male fertility is disrupted only following the application of a chemical protoxin. In one example of conditional male sterility, a gene encoding an N-acetyl-L-omithine deacetylase has been described that catalyzes the conversion of the protoxin N-acetyl-L-phosphinothricin into the herbicidal toxin L-phosphinothricin (Kriete et al., Plant Journal 9:809–818 (1996); EP 531,716 A2 (1992)). Transgenic plants expressing this gene in the tapetal cells of the anther were rendered male sterile only when treated with the N-acetyl-L-phosphinothricin protoxin. In another example of conditional male sterility, a gene encoding a bacterial cytochrome P450 has been described that catalyzes the conversion of a sulfonylurea protoxin R7402 into a herbicidal toxin (WO 91/03561; O'Keefe et al., Plant Physiology 105:473–482 (1994)). Transgenic plants expressing this gene in the tapetal cells of the anther were rendered male sterile only when treated with the R7402 protoxin. In another example of conditional male sterility, a gene encoding a phosphonate monoester hydrolase has been described that catalyzes the conversion of the protoxin glyceryl glyphosate into the herbicidal toxin glyphosate (Dotson, et al., Plant J. 10: 383–392(96)). Transgenic plants expressing this gene in the tapetal cells of the anther were rendered male sterile only when treated with the glycerol glyphosate protoxin.

Any of the sources of male sterility described above or known in the art could be employed in the present invention. This includes any naturally-occurring male sterile genetic system or by transforming a chimeric or recombinant gene into the female parent line of interest.

According to the invention, viable seed formation is prevented on the conditional female sterile plant (male parent plant) as a result of the conversion of the protoxin to the toxin in the female reproductive structures, and pollen production is prevented on the male sterile plant (female parent plant). To obtain hybrid seed, homozygous seed of the male parent and the female parent are interplanted in a production field thus allowing efficient pollen transfer. In one example of using the present invention to produce hybrid seed, the female parent is male sterile by any means and the male parent is engineered to be female sterile in the presence of an appropriate exogenously-applied protoxin. After application of the protoxin at the appropriate time during plant development, the only viable seed production will be a result of the male parent (female sterile) pollen fertilizing the female parent (male sterile) ovules. In the preferred mode of using the present invention, the female parent is engineered to be male-sterile upon application of a protoxin whereas the male parent is engineered to be female sterile in the presence of the same protoxin. To produce hybrid seed, the two parent lines are interplanted, and after application of the protoxin at the appropriate time during plant development, only hybrid seed is obtained. By these means any desired hybrid seed may be produced.

To produce hybrid wheat seed, the male parent is engineered to be female sterile in the presence of an appropriate exogenously-applied protoxin and the female parent is engineered to be male sterile in the presence of the same protoxin. Both transgenic parent lines are made homozygous and the seed multiplied by standard practices of the industry. For hybrid seed production, homozygous seed of the engineered male and female parent lines are interplanted at a ratio of males to females determined to assure efficient pollination. At an appropriate time during plant development, the protoxin is applied to the production field. Following seed maturation, the entire production field is harvested, yielding only hybrid seed.

EXAMPLES

The following examples further describe the materials and methods used in carrying out the invention and the subsequent results. They are offered by way of illustration, and their recitation should not be considered as a limitation of the claimed invention.

Example 1

Tobacco Plants which are Conditional for Female Sterility

Plasmid pSH58 was constructed containing the ΔS13 promoter (−339 to −79 of the $SLG_{13}$ promoter fused to −46 to +8 of the CaMV 35S promoter, Dzelkalns et al. Plant Cell 5: 855–863 (1993)) and fused to argE gene (SEQ ID NO:3) in the correct translational reading frame. The ΔS13 promoter is a female-preferential promoter.

The argE gene was obtained from E.coli genomic DNA by PCR reactions with primer 5'-TATCTAGACCAGAGGTGTGTCAACAAATGAA-3' (SEQ ID NO:5) and primer 5'-CGTCTAGATTGCGGCACTGGAGTTTC-3' (SEQ ID NO:6). The resulting fragment was cloned into pGEM-TA (Strategene) and the correct sequence was confirmed. Using a series of PCR and subcloning steps, a plant translational consensus sequence and a BamHI site was placed upstream of the argE translational start site using PCR primers, 5'CGCGGATCCTAAACAATGAAAAACAAATTACCGCC-3' (SEQ ID NO:7) and GCGCCTAGGCGCTTAATGCCAGCAAAAATCC-3' (SEQ ID NO:8). This product was then fused downstream of the ΔS13 promoter in plasmid $pSH_{15}$ (ΔS13 promoter in bluescript sk) and the nos transcriptional terminator added 3' to the β-glucuronidase (GUS) gene. This ΔS13-argE-nos cassette was then ligated as an EcoR1 fragment into pCIB200 containing T-DNA borders and a functional plant selectable marker, kanamycin resistance. This plasmid was designated pSH58.

Plasmid pFA100 is constructed in a manner similar to pSH58, above, except that the argE gene (SEQ ID NO:3) replaces the GUS gene in Stig1-GUS (Goldman et al., EMBO J. 13:2976–2984 (1994)) in the correct translational reading frame using appropriate restriction enzymes. The STIG1-argE fusion is then ligated into a vector such as pCIB200 containing T-DNA borders, 3' termination sequences and a functional plant selectable marker such as kanamycin resistance. The Stig1 promoter is a female-preferential promoter.

Tobacco leaf discs are transformed as described in Horsch et al., Science 227:1229–1231 (1985) with pSH58. The presence of the integrated transgenes is confirmed by PCR. Northern analysis of RNA made from female tissue is used to confirm tissue-specific expression of the argE gene in the transgenic plants. These plants are self-fertile and have the phenotype of conditional female sterility. T1 seed is collected after self-pollination. The female conditional transgene in pFA100 is also introduced into tobacco using similar procedures.

Example 2

Tobacco Plants which are Conditional for Male Sterility

Plasmid pSH60 was constructed with the TA29 promoter (Kriete et al., Plant J. 9:809–818 (1996)) fused to the argE gene. The TA29 promoter was cloned from tobacco by PCR using the primers 5'-AACTGCAGCTTTTGGTTAGCGA-ATGC-3' (SEQ ID NO:9) and 5'-CAGACTAGTTTTAG-CTAATTTCTTTAAGTAAAAAC-3' (SEQ ID NO:10). By a series of subcloning steps, the TA29 fragment was fused upstream of argE containing the plant consensus translation sequence, as described in Example 1, and a nos transcriptional terminator added 3' to the argE gene. The TA29-argE-nos cassette was cloned between T-DNA borders into the plasmid pSGCGF1 which also contains the plant selectable marker hygromycin. The resulting plasmid was designated pSH60.

Tobacco leaf discs were transformed as described in Horsch et al., Science 227:1229–1231 (1985) with pSH60. The presence of the integrated transgenes is confirmed by PCR. Northern analysis of RNA made from female tissue is used to confirm tissue-specific expression of the argE gene in the transgenic plants. These plants are self-fertile and have the phenotype of conditional male sterility. Ti seed is collected after self-pollination.

Tobacco leaf discs are also transformed with pGK73, containing an expression cassette of the argE gene under the control of the TA29 promoter (Krete et al., Plant J. 9:809–818 (1996)) as described in Horsch et al., Science 227:1229–1231 (1985). The presence of the integrated transgenes are confirmed by PCR. Northern analysis of RNA made from anthers is used to confirm tissue-specific expression of the argE gene in the transgenic plants. These plants are self-fertile and have the phenotype of conditional male sterility. Seed of the $T_1$ generation is collected after self-pollination.

Example 3

Chemical Treatment of Transformed Tobacco Plants Confers Tissue-specific Sterility Seed of the $T_1$ generation from both conditional female sterile plants (transformed with pFA100) and conditional male sterile plants (transformed with pGK73) are planted in soil. Once plantlets have grown to a sufficient size, leaf tissue is analyzed by PCR for the presence of the argE transgene. PCR positive plants are transferred to the greenhouse. These plants are fully fertile in the absence of exogenously-applied protoxin. A subset of the conditional female sterile plants and a subset of the conditional male sterile plants are treated with the protoxin acetyl-PPT during the growing stages. As the result of the preferential conversion of protoxin to toxin, the treated conditional male sterile plants become male sterile and the conditional female sterile plants become female sterile. The untreated plants remain fully fertile. Pollen from the treated female sterile plants is collected and used to pollinate the pistils of treated male sterile plants, which are the female parent plants. Fertilization occurs and hybrid seed is produced on the male sterile plant.

Example 4

Obtaining DNA Clones of Novel Genes Preferentially Expressed in Female Reproductive Structure of Maize A silk specific cDNA fragment was first identified using Clontech's PCR-Select cDNA Subtraction Kit (Clontech cat. #K1804-1). PolyA mRNA was isolated from developing maize silk, whole tassel, leaf, and root tissues of maize inbred line CG(0526 following procedures outlined in the Poly(A) Quick mRNA Isolation Kit (Stratagene cat. #200348). cDNAs were synthesized from polyA mRNA of each tissue and divided into the "tester cDNA", in this case represented by the silk cDNAs, and the "driver cDNA" composed of equal quantities of tassel, leaf, and root cDNAs. The cDNA subtraction and PCR amplification was carried out as described in the user's manual. The PCR products were subcloned into a TA-cloning vector, pCRII (Invitrogen cat. #K2000-01). Each subclone was screened for tissue specificity in Northern blots with 5 $\mu$g of total mRNA from maize silk, tassel, leaf, and root tissue. Clone B200i, 145 bp in length, showed silk specific expression. The B200i silk specific cDNA fragment was used to screen a developing silk CDNA library. The silk cDNA library was constructed using polyA mRNA isolated from silks taken from ears 18 cm long, following the procedures detailed in Stratagene's Zap cDNA Gigapack II Gold Cloning kit (Stratagene cat. #200402). Clones hybridizing to the B200i probe were selected for sequence analysis. One clone, 772 bp in size, contained the B200i probe sequence. This clone, B200i4-2, was used as a probe on Northern blots containing 1 $\mu$g polyA mRNA from maize silk, tassel, leaf, and root tissue. Expression was detected only in silk. The sequence of cDNA clone B200i4-2 is set forth in SEQ ID NO:1.

In order to isolate the corresponding genomic region, the B200i4-2 cDNA was used as a probe to screen a Mo17 maize genomic library (Stratagene). Lambda clones were isolated which hybridized strongly to the B200i4-2 probe. Southern analysis and restriction mapping was used to identify genomic fragments containing the respective cDNA sequence with 5' and 3' regions. A ~6.5 Kb Bam HI fragment was isolated from one of the positive lambda clones and subcloned into Bluescript SK+ (Stratagene) and designated pSH64.

The genomic B200i4-2 clone, pSH64, containing the 5' and 3'regulatory regions was analyzed by sequence analysis. Computerized scanning was also used to identify putative promoter elements. The sequence of the 5' and 3'regulatory region of the female-preferential gene contained in genomic clone pSH64 is set forth in SEQ ID NO: 11. The pSH64 clone was deposited under the terms of the Budapest Treaty on Feb. 27, 1998 with the Agricultural Research Service, Patent Culture Collection (NRRL), Northern Regional Research Center, 1815 North University Street, Peoria, Ill. 61604, U.S.A. and assigned accession number NRRL B-21920.

A chimeric gene which is expressed in a preferential manner in female reproductive structures is constructed as follows. The 431 bp 5' regulatory region of B200i was amplified from pSH64 by PCR using the primers 5'-AAAACTGCAGGAATTCACTGCTGAGGGAGCGA-3' (SEQ ID NO:12) and 5'-GCGGGATCCTTCTTGCTGTAGTCCTCGACCACG-3' (SEQ ID NO:13) and cloned as a PstI-BamHI fragment into pSOG10 which contains GUS fused to the nos termination sequences. The B200i-GUS-nos cassette was then subcloned as an EcoRI fragment into pSH64 digested with EcoRI, effectively placing GUS-nos downstream of the full length B200i regulatory region (nucleotides 1-3790 of SEQ ID NO:1 1). This plasmid was designated pSH70.

The B200i regulatory region from pSH70, as described above was cloned as a BglII-BamHI fragment into BS-KS (Stratagene) and the 3' regulatory region of B200i from pSH64 was added downstream as an EcoRV fragment (nucleotides 4427–6397 of SEQ ID NO:11). This plasmid was designated pSH73. Plasmid pSH74 was constructed by a partial BamHI digestion of pSH73 and ligating in a DNA fragment containing argE (from example 1) at the BamHI site, effectively placing argE between the 5' and 3' regulatory regions of B200i.

Example 5

Obtaining cDNA Clones of Novel Genes Preferentially Expressed in the Female Reproductive Structure of Wheat A pistil specific cDNA fragment was isolated from UC703 wheat by using Genhunter's mRNA Differential Display method (Genhunter cat. #M502) as described in the kit's protocol. Primers used to identify the pistil specific cDNA fragment were AP-18 and $T_{12}$ CA. The fragment was subcloned into a pGEM-TA cloning vector (Promega cat. #A362A) and named P26. The P26 clone was used as a probe on Northern blots containing 5 μg total mRNA from wheat pistil, anther, leaf, and root tissue and tissue specificity confirmed. A wheat pistil cDNA library was constructed using pistils isolated from UC703 wheat following the procedures outlined in Stratagene's Zap cDNA GigaPack II Gold Cloning kit (Stratagene cat. #200402). Clones hybridizing to the P26 probe were selected for sequence analysis. One clone, P26-A4, was 881 bp in length and contained the 203 bp P26 sequence. Northern blots containing 5 μg of total mRNA from four developmental stages of pistils, A) boot, B) emerged, C) mature, and D) fertilized, as well as anther, leaf, and root were hybridized with the 881 bp P26-A4 probe. Predominate pistil expression was detected in the pistil with very minor expression detected in root.

A second pistil specific cDNA fragment was also isolated from UC703 wheat using procedures similar to those above. This fragment was subcloned into a pGEM-TA cloning vector (Promega cat. #A362A) and named P19. The P19 clone was used as a probe on Northern blots containing 5 μg total mRNA from wheat pistil, anther, leaf, and root tissue and tissue specificity confirmed. A wheat pistil cDNA library was constructed as described above. Clones hybridizing to the P19 probe were selected for sequence analysis. One clone, P19-QA, was 649 bp in length and contained the P19 sequence. Northern blots containing 5 μg of total mRNA from four developmental stages of pistils, A) boot, B) emerged, C) mature, and D) fertilized, as well as anther, leaf, and root were hybridized with the 649 P19-QA probe. Expression was demonstrated to be preferential to the pistil.

Example 6

Obtaining Genomic Clones of Novel Genes Preferentially Expressed in Female Reproductive Structures of Wheat and Identifying the Promoter Region In order to isolate the corresponding genomic region, the P26-A4 cDNA was used as a probe to screen a custom UC703 wheat genomic library prepared from 2 week old seedlings. The library was constructed by partial MboI digestion of total genomic DNA and subsequent ligation of the 8–22 kb size fraction with BamHI-digested lambda EMBL3 DNA (Clontech Cat. #CS1013j). Lambda clones were isolated which hybridized strongly to the P26-A4 probe. Southern analysis and restriction mapping was used to identify genomic fragments containing the respective cDNA sequence with 5' and 3' regions. A 5.5 kb XbaI fragment was isolated from one of the positive lambda clones and subcloned into Bluescript SK+ (Stratagene). This was designated pCIB10302. The P26-A4 clone was deposited under the terms of the Budapest Treaty on Mar. 18, 1997 with the Agricultural Research Service, Patent Culture Collection (NRRL), Northern Regional Research Center, 1815 North University Street, Peoria, Ill. 61604, U.S.A. and assigned accession number NRRL B-21655N.

The genomic P26-A4 clone, pCIB 10302, containing the 5'regulatory regions was analyzed by sequence analysis. Computerized scanning is also used to identify putative promoter elements. Further, the 5' regions are mapped by endonuclease restriction enzymes and the transcription start site is determined by RACE PCR and RNAse protection methods. The sequence of the 5' regulatory region of the female-preferential gene contained in genomic clone P26-A4 is set forth in SEQ ID NO:2.

In order to isolate the corresponding genomic region, the P19 cDNA was used as a probe to screen a custom UC703 wheat genomic library prepared from 2 week old seedlings as described in example 6. Lambda clones were isolated which hybridized strongly to the P19 probe. Southern analysis and restriction mapping was used to identify genomic fragments containing the respective cDNA sequence with 5' and 3' regions. A ~8 Kb XhoI fragment was isolated from one of the positive lambda clones and subcloned into Bluescript SK+ (Stratagene), designated X2-1.

The genomic P19 clone containing the 5' and 3' regulatory regions was analyzed by sequence analysis. Computerized scanning was also used to identify putative promoter elements. Further, the 5' and 3' regions were mapped by endonuclease restriction enzymes.

The sequence of the 5' regulatory region of the female-preferential gene contained in genomic clone X2-1 is set forth in SEQ ID NO: 14. The X2-1 clone was deposited under the terms of the Budapest Treaty on Aug. 13, 1998 with the Agricultural Research Service, Patent Culture Collection (NRRL), Northern Regional Research Center, 1815 North University Street, Peoria, Ill. 61604, U.S.A. and assigned accession number NRRL B-21919 2N.

Example 7

Constructing Chimeric Genes which are Expressed in a Preferential Manner in Female Reproductive Structures Plasmid pFA200 was constructed by operably linking, using standard methods known in the art, the following components: 1) the P26 regulatory regions, as described above (nts 1-3987), 2) a DNA fragment containing the argE gene engineered with appropriate restriction sites to fuse the ATG of the open reading frame of argE in frame with the translational start site (ATG at nt 3987) of the P26 fragment, thereby fusing the upstream regulatory region of P26 with argE and 3) a vector containing 3' termination sequences which are functional in plants. Expression of argE under the control of the P26 promoter will express the argE gene product preferentially in the female reproductive structure of the plant.

The P19 5' regulatory regions (nucleotides 1–1093 of SEQ ID NO:14), cut with Pst I, a restriction enzyme site found just upstream of the P19 sequences in the X2-1 plasmid, and NcoI (nucleotide 1088 of SEQ ID NO:14) at the ATG of P19, was ligated to pSOG15 cut with PstI and NcoI (pSOG15 contains the GUS gene and the nos terminator with a PstI site 5' to the GUS gene and Nco I at the ATG of the GUS gene). This plasmid was designated pXB1.

Plasmid p19arg is constructed by operably linking, using standard methods known in the art, the following components: 1) the P19 regulatory regions, as described above, 2) a NA fragment containing the argE gene engineered with appropriate restriction sites to fuse ATG of the open reading frame of argE in frame with the translational start site (ATG at 1090 of SEQ ID NO:14) of the P19 fragment, thereby fusing the upstream regulatory region of P19 with argE and 3) a vector containing 3' termination sequences which are functional in plants. Expression of argE under the control of the P19 promoter will express the product argE gene product preferentially in the female reproductive structure of the plant.

Transient expression of genes in female reproductive structures was determined by delivery to intact tissues. Wheat floral tissue (pistils and anthers) was plated on Murashige and Skoog medium containing 15% maltose. DNA of pXB1 or pSH70 was precipitated onto micrometer size gold particles using standard procedures. Two target plates with 20 pistils and anthers per target were shot 2 or 3 times with the DuPont Biolistics® helium device using a burst pressure of 1100 psi. The plates were shot with an 80 mesh screen in place between the carrier stage and the target. The targets were placed in the dark at 26C for 16 hours after bombardment before the tissues were transferred to GUS development mix (100 mg X-gluc in 200 ml 0.05M sodium phosphate pH 7) for 2 to 24 hours at 37° C. The GUS genes in pXB1 and pSH70 produced GUS activity in the pistils. Transient transformation assays of pSH70 into maize silk tissue demonstrated expression of GUS in the female tissues.

Example 8

Transformation of Wheat with a Chimeric Gene which Encodes a Protein Catalyzing the Conversion of a Protoxin to a Toxin in a Female-Preferential Manner Immature embryos (0.75–1.0 mm length) of genotype UC703 are plated on Murashige and Skoog medium containing 3 mg/l 2,4-D and 3% sucrose. After approximately 4 hours the embryos are plated with the embryo axis side down onto plates containing Murashige and Skoog medium with 15% maltose, 3% sucrose and 3 mg/l 2,4-D overlaid with a filter paper supported slab of agarose containing the same components. The embryos are allowed to plasmolyze for 2–3 hours before bombardment.

DNA of pFA200 and pSOG35 is precipitated onto micrometer size gold particles using standard procedures. Four target plates with 20 embryos per target are shot twice with the DuPont Biolistics® helium device using a burst pressure of 1100 psi. The plates are shot with an 80 mesh screen in place between the carrier stage and the target. The targets are placed in the dark at 26C for 24 hours after bombardment before the slabs with the embryos are laid onto plates containing Murashige and Skoog medium with 3 mg/l 2,4-D and 3% sucrose. The individual embryos are removed from the slabs and placed directly on fresh medium of the same composition after another 48 hours.

Approximately 6 weeks after gene delivery, the responding tissue is placed on Murashige and Skoog medium with 3 mg/l 2,4-D and 3% sucrose with 0.2 mg/l methotrexate for a 3 week period. The tissue is then placed on a regeneration medium comprised of Murashige and Skoog medium with 1 mg/l zeatin riboside and 1 mg/l methotrexate. After 2 weeks, regenerating plantlets are placed in sterile containers called "GA7s" with half-strength Murashige and Skoog salts, 2% sucrose, 1 mg/l NAA and either 4 or 8 mg/l methotrexate.

In another example, immature embryos (0.75–1.0 mm length) of genotype UC703 are processed as described above, except that Murashige and Skoog medium containing 2 mg/l 2,4-D is used. After approximately 4 hours the embryos are plated with the embryo axis side down onto plates containing Murashige and Skoog medium with 15% maltose, 3% sucrose and 2 mg/l 2,4-D overlaid with a filter paper supported slab of agarose containing the same components. The embryos are allowed to plasmolyze for 2–3 hours before bombardment.

DNA of pFA200, pSH74 or p19arg, along with pUbi-Hyg containing the maize ubiquitin promoter operably linked to the hygromycin phosphotransferase gene, is precipitated onto micrometer size gold particles using standard procedures. Four target plates with 20 embryos per target are shot twice with the DuPont Biolistics® helium device using a burst pressure of 1100 psi. The plates are shot with an 80 mesh screen in place between the carrier stage and the target. The targets are placed in the dark at 26C for 24 hours after bombardment before the slabs with the embryos are laid onto plates containing Murashige and Skoog medium with 2 mg/l 2,4-D and 3% sucrose.

Approximately 3 weeks after gene delivery, the responding tissue is placed on Murashige and Skoog medium with 3 mg/l 2,4-D and 3% sucrose. The tissue is then placed on a regeneration medium comprised of Murashige and Skoog medium 3% sucrose, 5 mg/l GA3, 1 mg/l NAA and 20 mg/l hygromycin. After 2 weeks, regenerating tissue are transferred on medium comprised of Murashige and Skoog medium with 3% sucrose and 20 mg/l hygromycin. After 2 weeks, the regenerating plantlets are placed in sterile containers called "GA7s" with half-strength Murashige and Skoog salts, 2% sucrose, 1 mg/l NAA nad 20 mg/l hygromycin.

DNA is extracted from leaf tissue of plants derived from transformation and PCR is or the presence of the dhfr or hyg selectable marker genes and the argE gene. The PCR positive plants are sent to the greenhouse for propagation. During stages of flowering, pistils are collected from each transgenic plant and RNA made from this tissue. Expression of argE is confirmed by Northern analysis. Plants are self-fertilized and seed is collected.

Example 9

Constructing Chimeric Genes which are Expressed in a Preferential Manner in Male Reproductive Structures Plasmid pGK73 is used as a starting point. The TA29-argE-3' termination sequences are removed as a cassette from the Agrobacterium transformation vector and ligated into pBluescript KS+ using appropriate restriction enzymes. The resulting plasmid is referred to as pMA200.

The anther specific promoter, B6, was constructed from plasmid, pSGBNE1, which contains a 3 kb genomic clone subcloned as an EcoRI-NheI fragment from pSGB6g1 (see U.S. Pat. No. 5,470,359). A 1558 bp ApaI I/XbaI fragment was blunt cloned into Bluescript (KS) at the Sma I site. A translational fusion to the argE gene was constructed as previously described in Example 2. The resulting plasmid is referred to as pSH68.

The pollen specific promoter Zmg, a 1 kb HindIII-PpuMI fragment of Zmg13 (Hamilton et al. Sexual Plant Reproduction 2, 208–212 (1989)) was cloned from pCIB391 into bluescript as a HindIII-SmaI fragment. The nos transcription termination region was added as a BamHI-XbaI fragment. The coding sequence for argE as a BamHI fragment (from Example 1) was then ligated in at the BamHI site, effectively placing argE between the Zmg promoter and the nos termination sequences. This plasmid is referred to as Zmgarg.

Example 10

Transformation of Wheat with a Chimeric Gene which Expresses in a Male Preferential Manner Plasmids pUbi-Hyg, containing the maize ubiquitin promoter operably linked to the hygromycin phosphotransferase gene, and pMA200 or pSH68 or pZmgarg are used as the recombinant sequences for transformation of wheat immature embryos as described in Example 8. Plants are regenerated and PCR is used to confirm the presence of the argE transgene. Transgenic plants are transferred to the greenhouse. During stages of flowering, anthers are collected and RNA made from this tissue and argE expression is confirmed by Northern analysis. Plants are self-fertilized and seed is collected.

Example 11

Transformation of Maize with a Chimeric Gene which Encodes a Protein Catalyzing the Conversion of a Protoxin to a Toxin in a Female Preferential Manner Type I callus is obtained from immature zygotic embryos of genotype CG00526 using standard culture techniques. For gene delivery, approximately 300 mg of the Type I callus is prepared by chopping with a scalpel blade, rinsing 3 times with standard culture media containing 18% sucrose and immediately placed onto semi-solid culture medium again containing 18% sucrose. After approximately 4 hours, the tissue is bombarded using the PDS-1000/He Biolistic device from BioRad. One of the following plasmids: pFA200, pSH74 or p19arg, along with pSOG35, is precipitated onto 1 $\mu$m gold particles using the standard protocol from Bio-Rad. Approximately 16 hours after gene delivery the callus is transferred to standard culture medium containing 2% sucrose and 2 mg/L methotrexate. The callus is subcultured on selection for 8 weeks, after which surviving and growing callus is transferred to standard regeneration medium for the production of plants. Plants are obtained and given event numbers. Plants from each event are assayed by PCR for the presence of the argE gene and PCR positive plants are transferred to the greenhouse. During flowering, ears are collected, RNA is made from this tissue and expression of argE is confirmed by Northern analysis.

Alternatively, the transgenic maize plants are obtained by microprojectile bombardment of immature embryos. Ears of genotype CG00526 are self-pollinated and immature zygotic embryos are obtained approximately 10 days later. Approximately eight hundred and forty immature zygotic embryos are divided among 14 different target plates containing a medium capable of inducing and supporting the formation of embryogenic callus. The immature zygotic embryos are transferred immediately to the same medium but containing 12% sucrose. After 5 hours, the immature zygotic embryos are bombarded with either pFA200 or pSH74 or p19arg, along with pSOG35, using the PDS-1000/He device from BioRad. The plasmids are precipitated onto 1 $\mu$m gold particles essentially according to the published procedure from BioRad, as described above. The particles are delivered using a burst pressure of 1550 psi of helium. Each target plate is shot twice with the plasmid and gold particle preparation. The selection agent, methotrexate is applied at 2 mg/L on the day of gene delivery and increased to after approximately one month. The embryogenic callus so obtained is regenerated in the presence of the selection agent methotrexate. Plants are obtained and given event numbers. Plants from each event were assayed by PCR for the presence of the argE gene and PCR positive plants are transferred to the greenhouse. During flowering, ears are collected, RNA is made from this tissue and expression of argE is confirmed by Northern analysis.

Example 12

Transformation of Maize with a Chimeric Gene which Encodes a Protein Catalyzing the Conversion of a Protoxin to a Toxin in a Male Preferential-Specific Manner Plasmids pMA200 or pSH68 or pZmgarg and pSOG35 are used as the recombinant sequences for transformation of maize immature embryos as described in Example 11. Plants are regenerated and PCR is used to confirm the presence of the argE transgene. Transgenic plants are transferred to the greenhouse. During stages of flowering, tassels are collected, RNA is made from this tissue and argE expression is confirmed by Northern analysis. Plants are self-fertilized and seed is collected.

Example 13

Transformation of Barley which Encodes a Protein Catalyzing the Conversion of a Protoxin to a Toxin in a Female Preferential Manner Barley spikes (cv Golden Promise) with immature embryos about 1.5 to 2.5 mm in size are harvested, surface sterilized in 15% (v/v) bleach (5.25% sodium hypochlorite) for 10 minutes, and rinsed five times with sterile water. Immature embryos are dissected from young caryopses and bisected longitudinally. They are plated on a callus induction medium (Wan and Lemaux, Plant Physiology 104:37–48 (1994)) containing Murashige and Skoog basic salts supplemented with 30 g/L maltose, 1 mg/L thiamine-HCl, 0.25 g/L myo-inositol, 1 g/L casein hydrolysate, 0.69 g/L proline, 2.5 mg/L dicamba, and solidified by 3.5 g/L Phytagel®(Sigma).

For embryo bombardment, embryos are incubated scutellum-side up in the dark at 24–28° C. for 1–3 days. On the day of transformation, embryos are placed in the center of a petri dish (100×15 mm) to form a ring. DNA from plasmids pFA200 or pSH74 or p19arg, along with pUbi-hyg, are precipitated onto 0.6 or 1.0 micrometer gold particles (Bio-Rad) following the DuPont Biolistic Particle Delivery Systems manual. Each plate of embryo is shot once with a DuPont PDS-1000 helium gun using a burst of pressure at 1100 psi. After bombardment, the embryos are transferred to a fresh callus induction medium scutellum-side down. Three to seven days after bombardment, embryos are transferred to a selection medium (callus induction medium plus 10 mg/l hygromycin) for approximately 14 days. The derived callus is broken into smaller pieces and maintained separately. In subsequent subcultures, callus is transferred to a fresh selection medium with 20 mg/l hygromycin approximately every 21 to 28 days. After 2–3 subcultures, the surviving callus is transferred to a FHG medium (Hunter, Ph.D. thesis, Wye College, University of London, Ashford, Kent, 1988) supplemented with 1–3 mg(L 6-benzyl-aminopurine and 10–20 mg/l hygromycin for plant regeneration. Plants are regenerated at 23–25° C. under fluorescent lights. The emerged green shoots/plantlets are transferred to a Murashige and Skoog basic salts-based hormone-free medium in a 25×100 mm Petri dish. Plants are transferred to a Magenta GA7 container for further development when they reach 2–3 cm in size.

For callus bombardment, embryos are incubated scutellum-side down in the dark at 24–28° C. for at least 10 days. On the day of transformation, embryogenic callus from the cultured embryos are cut into small pieces and placed in the center of a petri dish. DNA delivery and the subsequent plant regeneration steps are identical as those described in embryo bombardment.

Plants are assayed by PCR for the presence of the transgene and those that are positive are transferred to the greenhouse. During stages of flowering, pistils are collected and RNA made from this tissue. Expression of argE expression is confirmed by Northern analysis. Plants are self-fertile and seeds are harvested.

Example 14

Transformation of Barley with a Chimeric Gene which Encodes a Protein Catalyzing the Conversion of a Protoxin to a Toxin in a Male Preferential Manner Plasmids pMA200 or pSH68 or pZmgarg and pUbi-Hyg are used as the recombinant sequences for transformation of barley immature embryos and callus as described in Example 13. Plants are regenerated and PCR is used to confirm the presence of the argE transgene. Transgenic plants are transferred to the greenhouse. During stages of flowering, anthers are collected and RNA made from this tissue and argE expression is confirmed by Northern analysis. Plants are self-fertilized and seed is collected.

Example 15

Chemical Treatment of Transformed Plants Confers Conditional Sterility

Seed from the $T_1$ generation from plants transformed with pFA200 or pSH74 or p19arg (conferring conditional female sterility) and plants transformed with pMA200 or pSH68 or pZmgarg (conferring conditional male sterility) are planted in soil. Once plantlets have grown to a sufficient size, leaf tissue is analyzed by PCR for the presence of the argE transgene. PCR positive plants are transferred to the greenhouse. These plants are fully fertile. A subset of the plants containing pFA200 or pSH74 or p19arg and a subset containing pMA200 or pSH68 or pZmarg are treated with the protoxin acetyl-PPT during the growing stages. The plants transformed with pMA200 or pSH68 or pZmgarg (homozygotes are needed for the pollen promoter construct Zmgarg) are male sterile as a result of the conversion of the acetyl-PPF to PPT in the male reproductive structures. The plants transformed with pFA200 or pSH74 or p19arg are female sterile as a result of the conversion of the acetyl-PPT to PPIT in the female reproductive structures. The untreated plants transformed with pFA200 or pSH74 or p19arg and pMA200 or pSH68 or pZmgarg are fully fertile.

Example 16

Producing Hybrid Seed of Wheat Using Transgenic Plants which Convert a Protoxin to a Toxin in Female Reproductive Structures Transgenic wheat plants from Examples 8 and 10 which were transformed with pFA200 or pSH74 or p19arg (conferring conditional female sterility) and pMA200 or pSH68 or pZmgarg (conferring conditional male sterility) are bred as plant lines homozygous for each of the transgenes and the seed is multiplied by standard practices. Homozygous seed from plants containing pFA200 or pSH74 or p19arg and plants containing pMA200 or pSH68 or pZmgarg are interplanted at a ratio of male to female parents sufficient to assure efficient pollen transfer. At an appropriate time during plant development, the protoxin acetyl-PPT is applied to the field. Following seed maturation, the entire production field is harvested, yielding only hybrid seed.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

---

We claim:

1. An expression cassette comprising a promoter isolatable from the maize B200i4-2 clone operatively linked to a heterologous coding sequence of interest.
2. The expression cassette of claim 1, wherein said coding sequence of interest encodes an enzyme which catalyzes the conversion of a protoxin to a toxin.
3. An expression cassette comprising a promoter isolatable from the wheat P26 clone operatively linked to a heterologous coding sequence of interest.
4. The expression cassette of claim 3, wherein said coding sequence of interest encodes an enzyme which catalyzes the conversion of a protoxin to a toxin.
5. An expression cassette comprising a promoter isolatable from the wheat P19 clone operatively linked to a heterologous coding sequence of interest.
6. The expression cassette of claim 5, wherein said coding sequence of interest encodes an enzyme which catalyzes the conversion of a protoxin to a toxin.
7. A plant comprising the expression cassette according to claim 1.
8. A plant comprising the expression cassette according to claim 2.
9. A plant comprising the expression cassette according to claim 3.
10. A plant comprising the expression cassette according to claim 4.
11. A plant comprising the expression cassette according to claim 5.
12. A plant comprising the expression cassette according to claim 6.
13. Seed of the plant according to claim 7, wherein said seed comprises the expression cassette.
14. Seed of the plant according to claim 8, wherein said seed comprises the expression cassette.
15. Seed of the plant according to claim 9, wherein said seed comprises the expression cassette.
16. Seed of the plant according to claim 10, wherein said seed comprises the expression cassette.
17. Seed of the plant according to claim 11, wherein said seed comprises the expression cassette.
18. Seed of the plant according to claim 12, wherein said seed comprises the expression cassette.
19. An isolated female-preferential promoter from the genomic B200i4-2 clone having the accession number NRRL B-21920.
20. The female-preferential promoter of claim 19, wherein said promoter is comprised of nucleotides 1 to 1390 of SEQ ID NO:11.
21. An isolated female-preferential promoter from the genomic P26 clone having the accession number NRRL B-21655N.
22. The female-preferential promoter of claim 21, wherein said promoter is comprised of the sequence set forth in SEQ ID NO:2.
23. An isolated female-preferential promoter from the genomic P19 clone having the accession number NRRL B-21919 2N.
24. The female-preferential promoter of claim 23, wherein said promoter is comprised of nucleotides 1 to 1093 of SEQ ID NO:14.
25. An expression cassette comprising the female-preferential promoter according to claim 19 operatively linked to a coding sequence of interest.
26. An expression cassette comprising the female-preferential promoter according to claim 20 operatively linked to a coding sequence of interest.
27. An expression cassette comprising the female-preferential promoter according to claim 21 operatively linked to a coding sequence of interest.
28. An expression cassette comprising the female-preferential promoter according to claim 22 operatively linked to a coding sequence of interest.
29. An expression cassette comprising the female-preferential promoter according to claim 23 operatively linked to a coding sequence of interest.
30. An expression cassette comprising the female-preferential promoter according to claim 24 operatively linked to a coding sequence of interest.
31. A plant comprising the expression cassette according to claim 25.
32. A plant comprising the expression cassette according to claim 26.
33. A plant comprising the expression cassette according to claim 27.
34. A plant comprising the expression cassette according to claim 28.
35. A plant comprising the expression cassette according to claim 29.
36. A plant comprising the expression cassette according to claim 30.
37. Seed of the plant according to claim 31, wherein said seed comprises the expression cassette.
38. Seed of the plant according to claim 32, wherein said seed comprises the expression cassette.
39. Seed of the plant according to claim 33, wherein said seed comprises the expression cassette.
40. Seed of the plant according to claim 34, wherein said seed comprises the expression cassette.
41. Seed of the plant according to claim 35, wherein said seed comprises the expression cassette.
42. Seed of the plant according to claim 36, wherein said seed comprises the expression cassette.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 772 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "cDNA sequence for
          female-pref erential transcript designated B200i4-2"

(iii) HYPOTHETICAL: NO (xi) SEQUENCE DESCRIPTION: SEQ ID NO:1:

```
GTCCTACGTG GTCGAGGACT ACAGCAAGAA ATGGGGGTCT ACAAGTCTGC A GTTCTGCTT     60

GGTGTGGTTT TGGCCTCAGT CCTTCTCGGC TTCCTGGACG TTGTGTACGC A AGGGAGCTC    120

ACTGAAGCCA ATGGCTCTGG AGTGAAGAAT AATGTGAAGC CTGCAGGAGA G CCTGGGCTC    180

AAGGATGAGA AGTGGTTTGG TGGTGGATAC AAGCATGGTG GAGGGTATGG A AACAACCAG    240

CCAGGATACG GTGGCGGAGG AAACAGCCAA CCTGGATACG GCGGCGGAGG A AACAGTCAG    300

CCCGGATACG GTGGAGGATA CAAGCGCCAT CACCCTGGTG GCGGCTACGG G TCTGGACAA    360

GGAGGGCCTG GATGTGGATG TGGAGGAGGG TATGGAGGTG GCAATGGTAG T CCTGGGTAC    420
```

```
GGCGATGACA ATGGTGGTGG CAGTGGCACT GGTGGCGGAA ATGGCAATGC T GGTGGGTAC      480

GGAGGAGGAG GAGGCGGCGG TTATGGAGGC GGCTACGGCA GTGGTAGTGG T ACAGCACCA      540

GGAGGCGGAT ATCATGGCGG TGGTGGTGCA CAACGCTACG CTGGGCAAAA C TAGCAAGAA      600

CAACCCCTTA TGCTAGTTTA TGTTAAATAA ACGATCCATT GTTCATGTGA C TGAGCAATT      660

TAAGCAGTGA AGGATCTTGA CTCGTGTTAT TTGTGTTACC ATATGTATTG G TTGTTTTAT      720

GTTTAAGATG AATGTACACC GCTATTTGTA AAAAAAAAAA AAAAAAAAA A A              772

(2) INFORMATION FOR SEQ ID NO:2:

(i) SEQUENCE CHARACTERISTICS:
        (A) LENGTH: 4126 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: TATA_ signal
        (B) LOCATION: 3864

(ix) FEATURE:
        (A) NAME/KEY: misc_ feature
        (B) LOCATION: 3912
        (D) OTHER INFORMATION: /function= "transcription start
            site"

(ix) FEATURE:
        (A) NAME/KEY: misc_ feature
        (B) LOCATION: 3983
        (D) OTHER INFORMATION: /function= "ATG site used for
            translation al fusions"

(xi) SEQUENCE DESCRIPTION: SEQ ID NO:2:

TCTAGATTAT TGAATCTAGT GCATGTGGGA GACTGAAGGA AATATGCCCT A GAGGCAATA       60

ATAAAGTTGT TATTTACATT TCCTTATATC ATGATAAATG TCTATTATTC A TGCTAGAAT      120

TGTATTAACC AGAAACTTGA TACATGTGTG GATACATAGA CAAAACACAG T GTCCCTAGT      180

AAGCCTCTAC TAGATTAGCT CGTTAATCAA AGATGGTTAA GTTTCCTAAC C ATATACATG      240

TGTTGTCATT TGATGAACGG GATCACATTA TTAGGAGAAT GATGTGATGG A CAAGACCCA      300

TCCGTTATCT TAGCATATTG ATCGTTCAGT TTTATTGCTA TTGCTTTCTT C ATGTCATAT      360

ACATATTCAT TTGACTATGA GATTATGCAA CTCCCGGATA CCAGAGGTAT A CCTTGTGTG      420

CTATCAAACA TCACAACATA ACTAGGTGAT TATAAAGATG CTCTACAGGA A TCTCCGAAG      480

GTGTTTGTTG GGTTAGCATA GATCGAGATT AGGATTTGTC ACTCCGAGTA T CATAGAGGT      540

ATATCTGGGC CCTCTCGGTA ATGCACATCA TAATAAGCCT TGTAAGCAAT G TGACTAATG      600

AGTTATTTGT GGGATGATGT ATTACGGAAC GACTAAAGAG ACTTGCCGGT A ACGAGATTG      660

AACTAGGTAT GAAGATACCG ACGATCGAAT CTCGGGCAAG TAACATACCG A TGACAAAGG      720

AAATAATGTA TGTTGTCATT ACGGTACGAC CGATAAAGAT CTTCATAGAA T ATGTGGGAA      780

CTAATATGAG CATCCAGGTT CCGCTGTTGG TTATTGACTG GAGAGGTGTC T CGGTCATGT      840

CTACATAATT CTCGAACTCG TAGGGTCCGC ACGCTTAACC TTCGATGACG A TTTTGTATT      900

ATATGAGTTG TGTCATTTGG TGACCGAATG TTGTTCGGAG TCCCGGATGA G ATCACAGAC      960

ATGACGAGGA GTCTCGAAAA TGTTGAGAGG TAAAGATTCA TATATTGTAC G ATGATATTC     1020

GGACACCGGA AGTATTCCGG GGGTACCGGG TACATATCGG GTCACCGGAA G GGGTTCTGG     1080
```

```
GCATCCCCCC GGCAATTACA TGGGCCTAAT GGGCCAAGAA GGGGACATAC C AGCCCCTAG    1140

GGGGCTGGTG CACCCCATGT AGGCCAAAAT AAGGGGAAG  GAAAGAAGTG G AAGATAGAA    1200

AGGAGGGGGA GCAATTCGGC CTCCCCCTTC CTTCTCTCCT CCCTCATCCT T CCTTCCCCC    1260

CTCGGATGAA TACGGAAGGG GGGAGGCCGA ATTGGGAGGC GCACAAGTAG G ATTCCTCCT    1320

ACTTGGGGCG CCCCCTTGGC TGCCTCTCCT CCCCTCCAAC CTATATATAT G AGGGGGCAC    1380

CGCTAGAACA CACACCAACC ATTGTTAGTC GTGTGCGGCG CCCCCCTCCA C AGTTTACGC    1440

CTCCGATCAT ATTCACATAG TGCTTAGGCG AAGCCCTGCG CGGATCACTT C ACCATTACT    1500

ATCACCACGC CAGTGTGCTG ACGGAACTAT CATTCGACAC TTTGCTAGAT C AAGAGTTCG    1560

AGGGACGTCA TCGAGTTGAA CGTGTGCAGA ACTCGGAGGT GCCGTACATT C GGTGCTTGA    1620

TCGGTCGGAA CGAGAAGAAG TTTGACGACA TCAACCGCGT TGTCAAACGC T TCCACTTTC    1680

GGTCTACGGG AGTACGTGGA CACACTCTCC CCCTCTCGTT GCTATGCATC T CCTAGATAG    1740

ATCTTGCGTG AGCGCAGGAA TTTTTTTGAA ATTGCATGCT ATGTTTCCCA A CACCAAGAT    1800

CTGGAGGGAG ATCCAAAGCA GCCGCCGCTT GTCGGCGTGG AAAACCATGA C TTCGGCATG    1860

GTGGCCACGG CGGATTGGGC GCCTAGAAGC AGAGAAGCTG GGAGCGAAGA A GAAGAGGAT    1920

CAAAGAGGTG CGGTGTGGAC GGCGCTGAGG CACGGCTTAA GTAGGCACGA C CAAGTGAAG    1980

GGACGGGAAG CTGGTTCCAA TGTTGTGCAG TGGCCGGAGT AGGTTTCTTG A TCGCCCCAT    2040

TGATGCGTGA AACTGCAACT AATCCCCTGA TGGTTTTGGT TATTCATAAC A ACATATGCA    2100

TCATTGAACT AATGCCTACT CAAAGAATAT TTCAAGAAAG TTCATTTATG T ATGGCAATG    2160

GGATGTGAAT GGGACCCCTC AAAATGCTAA AGGACAAACA TTGGCAAAGC T TCAAGAATC    2220

TACATTTTTG GTTAAGCGAT CCAAGATCAC AATGAGTCTA TAGAAAAGCC A ATACAATTA    2280

AAAGGGAATG AGGTTTTACT CATGGACTAC TTGCCCAAGT GCTTAGAGAT A TTGCTCCAA    2340

AACCCTCAGC CACACCCTCA CATTCATCTA TTTTCAAAAC CCTAAAGCCT A TCTCGGTCC    2400

CACCAAAACA CATCCAACCG GACCCACCAA GATACACTTG ACATAGTCGC T GCCTAAACC    2460

CAAGCAACTT GGTCCCACCG GGATGACCCT CCGGTCTCAC CGAAGAGCAC T TGCCAACCT    2520

TCTGTAACCT ATCATTTCAT CTCGGAAATT CCGAGAGGTT TCGATAGGTC T TAGCGAAGT    2580

GTGAAAAGTG ATTAGGTCAT CACCATTCGG TCTCACCGCA CTGTTCTATC C GGTCTCACC    2640

GAAAATTCTG AAGTTCAAAC CTTTTGTGCT AGTCGGCCTC ACCAAGTGAT T CATCCGGT    2700

CCCACTGAGT AGTGCATAAA GGTGTGTGCT TAGTGCCTAT ATATACGTCC A CCCATTCCA    2760

CCAACTCTCA GAGAGCAATC AGGACGAAAC TACCACTTCC CATATTCATT T TCTGAGAGA    2820

GAACCACCTG CACTTGTGTT GAAATCAAGG GGATTCCACT CCAACCTTTG A TCTTTGATT    2880

TCTATCCCCC TCAAGTGGCT TTCCACTCTA CTCATTCTCC TGCCACATAG C CAAATCTGT    2940

GAGAGAATGA TTGGGTGTTG AGGTGACTAT CTTTTGAAAC ACAAAAATAA G GAGTTCATC    3000

AGCAACAACA ACATCTATTA CCTTTGTGAG AGTGGTGTCT TCCAGATTGG T TAGGTGTCA    3060

CTTGGGAGCC TCCAAGATGT GGAGTTGAAC CAAGGAGTTT GTAAAGGTAA A GAGATCGCC    3120

TACTTCATGA AGATTTACCT GAGTGAGGCT AGTCCTTCAT GGGCGTAAGC C ATGGTGACA    3180

TAGATAAGGT TGCATTTGAT CTTCCAAACC CCCTCCTTTA TGTTCATATG C AAAGTCTTT    3240

ACTTTCTGCT GCCTACTAAC TTAGACTTGC ATGTATAGAG TGTGACAAGA C TTGTTAGAA    3300

TTGCCAAAAC TTGCCTAGAA TTAAAATTGG GAAAAGGTCA AGTTTTTACT T GCCAAGTAG    3360

TCTAATCCCC TCCCCCCTAC TAGACCTACT TGCGATCCTA CAAAGTGACG C CGCGCTCTA    3420

CTCCGGCCGC ATCACTCTGA AGCGGTGGTC ACCTGCATGA ATGCACGGTA A CCGCTTCTC    3480
```

-continued

| | |
|---|---|
| GTGGAGAGGG TTTTCGGGCA CAAGGGTTTT TGGGTGGGAC CGTGGTGTCG G GCGAGGGCG | 3540 |
| TGTATGTATC TGCAATCCGG TCGTTGTGTC CGGTTTGTGG AAAAACGGAC A ACCAGATCG | 3600 |
| GTCCACAGAT CAATAGGATA CTGCATTGGA TGGTAAATTT CATCTAAAGA C CGATGAGAT | 3660 |
| ACCGCGTTGA ATGATAAATT ACATCCTAAC TACCCGATCC AGATGATTGC A GACAGTTTA | 3720 |
| AGGGTCAGAG ATGCACTTAA TGGTCACCAT GAACAAACAT CTGCACCCCA C GCCATTCTC | 3780 |
| GCACTGGCCT CATTTACAGC CTCCCCATCT GCCCCGCTCG ACTCTCCATC G CACCATACG | 3840 |
| TACTCCCYTC CTCCTCCTCG GCCTATTTAA ACCGCAAGCT TCACCACACC A AATGCACTA | 3900 |
| GTAGGAACGA TCTCACGCGC AACACAAGAG AGAGCGAATA GAACCGACAT C CGTAGCTGG | 3960 |
| TTTGCTAGAC TAGAGCGGCG CCATGGCCAA GAAGGGCTCA GGCACTGCCG C CTCTCTCCT | 4020 |
| GCTCTGCCTC GCGCTGGCGG CGCACACCGT CGTGGCTGCC AGGACCATGC C CGCTGCAGC | 4080 |
| TGGCGGCGTG GCGGAAGCCT CACTTCCGGC CGCCGCCGCC ACGGAA | 4126 |

(2) INFORMATION FOR SEQ ID NO:3:

(i) SEQUENCE CHARACTERISTICS:
        (A) LENGTH: 2070 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION: 211..1362
        (D) OTHER INFORMATION: /product= "N-acetylornithinase"

(xi) SEQUENCE DESCRIPTION: SEQ ID NO :3:

| | |
|---|---|
| GGTCACTAGC TCTGCGCCAG CGTAGCCGCT GGCACCCACA ATCAGCGTAT T CAACATCGG | 60 |
| GGCTATTCAC CTTCTTATGT CTGGTTGCCA GGTTAAACGT AAAACATTCA C CTTACGGCT | 120 |
| GGTGGGTTTT ATTACGCTCA ACGTTAGTGT ATTTTTATTC ATAAATACTG C ATGAATATT | 180 |
| GATACTATCA TGACCAGAGG TGTGTCAACA ATG AAA AAC AAA T TA CCG CCA TTT | 234 |
|                                                           Met Lys Asn Lys Leu Pro Pro Phe | |
|                                                           1               5 | |
| ATC GAG ATT TAC CGC GCT CTG ATT GCC ACA C CT TCA ATA AGC GCC ACG | 282 |
| Ile Glu Ile Tyr Arg Ala Leu Ile Ala Thr P ro Ser Ile Ser Ala Thr | |
|       10                  15                   20 | |
| GAA GAG GCA CTC GAT CAA AGC AAT GCA GAT T TA ATC ACT CTG CTG GCG | 330 |
| Glu Glu Ala Leu Asp Gln Ser Asn Ala Asp L eu Ile Thr Leu Leu Ala | |
| 25                  30                      35                   40 | |
| GAC TGG TTT AAA GAT TTG GGC TTC AAT GTG G AA GTG CAG CCT GTT CCA | 378 |
| Asp Trp Phe Lys Asp Leu Gly Phe Asn Val G lu Val Gln Pro Val Pro | |
|                 45                     50                      55 | |
| GGA ACT CGC AAC AAA TTC AAT ATG CTG GCA A GT ATC GGA CAG GGG GCT | 426 |
| Gly Thr Arg Asn Lys Phe Asn Met Leu Ala S er Ile Gly Gln Gly Ala | |
|                    60                     65                      70 | |
| GGC GGC TTG TTG CTG GCG GGG CAT ACC GAT A CG GTG CCA TTT GAT GAC | 474 |
| Gly Gly Leu Leu Leu Ala Gly His Thr Asp T hr Val Pro Phe Asp Asp | |
|                       75                     80                          85 | |
| GGT CGC TGG ACG CGC GAT CCG TTT ACA CTG A CG GAG CAT GAC GGC AAG | 522 |
| Gly Arg Trp Thr Arg Asp Pro Phe Thr Leu T hr Glu His Asp Gly Lys | |
|                 90                     95                          100 | |
| CTT TAC GGC TTA GGC ACC GCC GAC ATG AAA G GC TTT TTT GCG TTT ATC | 570 |
| Leu Tyr Gly Leu Gly Thr Ala Asp Met Lys G ly Phe Phe Ala Phe Ile | |
| 105                    110                    115                    120 | |

```
CTT GAT GCG CTA CGC GAT GTC GAC GTC ACG A AA CTG AAA AAA CCG CTC        618
Leu Asp Ala Leu Arg Asp Val Asp Val Thr L ys Leu Lys Lys Pro Leu
                125                 130                 135

TAC ATT CTG GCG ACT GCT GAT GAA GAA ACC A GT ATG GCC GGA GCG CGT        666
Tyr Ile Leu Ala Thr Ala Asp Glu Glu Thr S er Met Ala Gly Ala Arg
                140                 145                 150

TAT TTT GCC GAA ACT ACC GCC CTG CGC CCG G AT TGC GCC ATC ATT GGC        714
Tyr Phe Ala Glu Thr Thr Ala Leu Arg Pro A sp Cys Ala Ile Ile Gly
                155                 160                 165

GAA CCG ACG TCA CTA CAA CCG GTA CGC GCA C AT AAA GGT CAT ATC TCT        762
Glu Pro Thr Ser Leu Gln Pro Val Arg Ala H is Lys Gly His Ile Ser
    170                 175                 180

AAC GCC ATC CGT ATT CAG GGC CAG TCG GGG C AC TCC AGC GAT CCA GCA        810
Asn Ala Ile Arg Ile Gln Gly Gln Ser Gly H is Ser Ser Asp Pro Ala
185                 190                 195                 200

CGC GGA GTT AAC GCT ATC GAA CTA ATG CAC G AC GCC ATC GGG CAT ATT        858
Arg Gly Val Asn Ala Ile Glu Leu Met His A sp Ala Ile Gly His Ile
                205                 210                 215

TTG CAA TTG CGC GAT AAC CTG AAA GAA CGT T AT CAC TAC GAA GCG TTT        906
Leu Gln Leu Arg Asp Asn Leu Lys Glu Arg T yr His Tyr Glu Ala Phe
                220                 225                 230

ACC GTG CCA TAC CCT ACG CTC AAC CTC GGG C AT ATT CAC GGT GGC GAC        954
Thr Val Pro Tyr Pro Thr Leu Asn Leu Gly H is Ile His Gly Gly Asp
                235                 240                 245

GCT TCT AAC CGT ATT TGC GCT TGC TGT GAG T TG CAT ATG GAT ATT CGT       1002
Ala Ser Asn Arg Ile Cys Ala Cys Cys Glu L eu His Met Asp Ile Arg
                250                 255                 260

CCG CTG CCT GGC ATG ACA CTC AAT GAA CTT A AT GGT TTG CTC AAC GAT       1050
Pro Leu Pro Gly Met Thr Leu Asn Glu Leu A sn Gly Leu Leu Asn Asp
265                 270                 275                 280

GCA TTG GCT CCG GTG AGC GAA CGC TGG CCG G GT CGT CTG ACG GTC GAC       1098
Ala Leu Ala Pro Val Ser Glu Arg Trp Pro G ly Arg Leu Thr Val Asp
                285                 290                 295

GAG CTG CAT CCG CCG ATC CCT GGC TAT GAA T GC CCA CCG AAT CAT CAA       1146
Glu Leu His Pro Pro Ile Pro Gly Tyr Glu C ys Pro Pro Asn His Gln
                300                 305                 310

CTG GTT GAA GTG GTT GAG AAA TTG CTC GGA G CA AAA ACC GAA GTG GTG       1194
Leu Val Glu Val Val Glu Lys Leu Leu Gly A la Lys Thr Glu Val Val
                315                 320                 325

AAC TAC TGT ACC GAA GCG CCG TTT ATT CAA A CG TTA TGC CCG ACG CTG       1242
Asn Tyr Cys Thr Glu Ala Pro Phe Ile Gln T hr Leu Cys Pro Thr Leu
                330                 335                 340

GTG TTG GGG CCT GGC TCA ATT AAT CAG GCT C AT CAA CCT GAT GAA TAT       1290
Val Leu Gly Pro Gly Ser Ile Asn Gln Ala H is Gln Pro Asp Glu Tyr
345                 350                 355                 360

CTG GAA ACA CGG TTT ATC AAG CCC ACC CGC G AA CTG ATA ACC CAG GTA       1338
Leu Glu Thr Arg Phe Ile Lys Pro Thr Arg G lu Leu Ile Thr Gln Val
                365                 370                 375

ATT CAC CAT TTT TGC TGG CAT TAA AACGTAGGCC G GATAAGGCG CTCGCGCCGC      1392
Ile His His Phe Cys Trp His  *
                380

ATCCGGCGCT GTTGCCAAAC TCCAGTGCCG CAATAATGTC GGATGCGATG C TTGCGCATC    1452

TTATCCGACC TACAGTGACT CAAACGATGC CCAACCGTAG GCCGGATAAG G CGCTCGCGC    1512

CGCATCCGGC ACTGTTGCCA AACTCCAGTG CCGCAATAAT GTCGGATGCG A TACTTGCGC    1572

ATCTTATCCG ACCGACAGTG ACTCAAACGA TGCCCAACTG TAGGCCGGAT A AGGCGCTCG    1632

CGCCGCATCC GGCACTGTTG CCAAACTCCA GTGCCGCAAT AATGTCGGAT G CGATACTTG    1692

CGCATCTTAT CCGACCTACA CCTTTGGTGT TACTTGGGGC GATTTTTTAA C ATTTCCATA    1752
```

```
AGTTACGCTT ATTTAAAGCG TCGTGAATTT AATGACGTAA ATTCCTGCTA T TTATTCGTT    1812

TGCTGAAGCG ATTTCGCAGC ATTTGACGTC ACCGCTTTTA CGTGGCTTTA T AAAAGACGA    1872

CGAAAAGCAA AGCCCGAGCA TATTCGCGCC AATGCGACGT GAAGGATACA G GGCTATCAA    1932

ACGATAAGAT GGGGTGTCTG GGGTAATATG AACGAACAAT ATTCCGCATT G CGTAGTAAT    1992

GTCAGTATGC TCGGCAAAGT GCTGGGAGAA ACCATCAAGG ATGCGTTGGG A GAACACATT    2052

CTTGAACGCG TAGAAACT                                                   2070
```

(2) INFORMATION FOR SEQ ID NO:4:

(i) SEQUENCE CHARACTERISTICS:
        (A) LENGTH: 383 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Asn Lys Leu Pro Pro Phe Ile Glu I le Tyr Arg Ala Leu Ile
  1               5                  10                  15

Ala Thr Pro Ser Ile Ser Ala Thr Glu Glu A la Leu Asp Gln Ser Asn
             20                  25                  30

Ala Asp Leu Ile Thr Leu Leu Ala Asp Trp P he Lys Asp Leu Gly Phe
         35                  40                  45

Asn Val Glu Val Gln Pro Val Pro Gly Thr A rg Asn Lys Phe Asn Met
     50                  55                  60

Leu Ala Ser Ile Gly Gln Gly Ala Gly Gly L eu Leu Leu Ala Gly His
 65                  70                  75                  80

Thr Asp Thr Val Pro Phe Asp Asp Gly Arg T rp Thr Arg Asp Pro Phe
                 85                  90                  95

Thr Leu Thr Glu His Asp Gly Lys Leu Tyr G ly Leu Gly Thr Ala Asp
            100                 105                 110

Met Lys Gly Phe Phe Ala Phe Ile Leu Asp A la Leu Arg Asp Val Asp
        115                 120                 125

Val Thr Lys Leu Lys Lys Pro Leu Tyr Ile L eu Ala Thr Ala Asp Glu
    130                 135                 140

Glu Thr Ser Met Ala Gly Ala Arg Tyr Phe A la Glu Thr Thr Ala Leu
145                 150                 155                 160

Arg Pro Asp Cys Ala Ile Ile Gly Glu Pro T hr Ser Leu Gln Pro Val
                165                 170                 175

Arg Ala His Lys Gly His Ile Ser Asn Ala I le Arg Ile Gln Gly Gln
            180                 185                 190

Ser Gly His Ser Ser Asp Pro Ala Arg Gly V al Asn Ala Ile Glu Leu
        195                 200                 205

Met His Asp Ala Ile Gly His Ile Leu Gln L eu Arg Asp Asn Leu Lys
    210                 215                 220

Glu Arg Tyr His Tyr Glu Ala Phe Thr Val P ro Tyr Pro Thr Leu Asn
225                 230                 235                 240

Leu Gly His Ile His Gly Gly Asp Ala Ser A sn Arg Ile Cys Ala Cys
                245                 250                 255

Cys Glu Leu His Met Asp Ile Arg Pro Leu P ro Gly Met Thr Leu Asn
            260                 265                 270

Glu Leu Asn Gly Leu Leu Asn Asp Ala Leu A la Pro Val Ser Glu Arg
        275                 280                 285
```

```
Trp Pro Gly Arg Leu Thr Val Asp Glu Leu His Pro Pro Ile Pro Gly
    290                 295                 300

Tyr Glu Cys Pro Pro Asn His Gln Leu Val Glu Val Val Glu Lys Leu
305                 310                 315                 320

Leu Gly Ala Lys Thr Glu Val Val Asn Tyr Cys Thr Glu Ala Pro Phe
                325                 330                 335

Ile Gln Thr Leu Cys Pro Thr Leu Val Leu Gly Pro Gly Ser Ile Asn
            340                 345                 350

Gln Ala His Gln Pro Asp Glu Tyr Leu Glu Thr Arg Phe Ile Lys Pro
                355                 360                 365

Thr Arg Glu Leu Ile Thr Gln Val Ile His His Phe Cys Trp His
    370                 375                 380
```

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer for argE"

(iii) HYPOTHETICAL: NO (xi) SEQUENCE DESCRIPTION: SEQ ID NO:5:

TATCTAGACC AGAGGTGTGT CAACAAATGA A                         31

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer for argE"

(iii) HYPOTHETICAL: NO (xi) SEQUENCE DESCRIPTION: SEQ ID NO:6:

CGTCTAGATT GCGGCACTGG AGTTTC                             26

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer for argE"

(iii) HYPOTHETICAL: NO (xi) SEQUENCE DESCRIPTION: SEQ ID NO:7:

CGCGGATCCT AAACAATGAA AAACAAATTA CCGCC                    35

(2) INFORMATION FOR SEQ ID NO:8:

(i) SEQUENCE CHARACTERISTICS:
        (A) LENGTH: 31 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "primer for argE"

(iii) HYPOTHETICAL: NO (xi) SEQUENCE DESCRIPTION: SEQ ID NO:8:

GCGCCTAGGC GCTTAATGCC AGCAAAAATC C                                31

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer for TA29"

(iii) HYPOTHETICAL: NO (xi) SEQUENCE DESCRIPTION: SEQ ID NO:9:

AACTGCAGCT TTTTGGTTAG CGAATGC                                     27

(2) INFORMATION FOR SEQ ID NO:10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer for TA29"

(iii) HYPOTHETICAL: NO (xi) SEQUENCE DESCRIPTION: SEQ ID NO:10:

CAGACTAGTT TTAGCTAATT TCTTTAAGTA AAAAC                            35

(2) INFORMATION FOR SEQ ID NO:11:

(i) SEQUENCE CHARACTERISTICS:
        (A) LENGTH: 6596 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: promoter
        (B) LOCATION: 1..3790
        (C) IDENTIFICATION METHOD : experimental
        (D) OTHER INFORMATION: /function= "5' Regulatory Region of
            B200i4-2"
            /evidence= EXPERIMENTAL (ix) FEATURE:
        (A) NAME/KEY: misc_ signal
        (B) LOCATION: 4427..6397
        (C) IDENTIFICATION METHOD : experimental
        (D) OTHER INFORMATION: /function= "3' Regulatory Region
            for B200 i4-2"
            /evidence= EXPERIMENTAL
```

```
    (ix) FEATURE:
         (A) NAME/KEY: misc_ feature
         (B) LOCATION: 3789..3791
         (D) OTHER INFORMATION: /function= "ATG translation start"

(ix) FEATURE:
         (A) NAME/KEY: misc_ feature
         (B) LOCATION: 4402..4404
         (D) OTHER INFORMATION: /function= "translation stop"

(xi) SEQUENCE DESCRIPTION: SEQ ID NO:11:

GGATCCTTAG ATCTTTAGGT GCACGTTAGT TACTGGAAAT GTAAACACAA C AGGAATAGG       60

TGAAGCGACA ATGGACAACA CATGACGACT CTCAAGTGGT TACCTCAAAC A GCCAAAGCA     120

CAATTTTCGA TGCAAGAACT AGATGCAAAG AGCTACTAAC AAAGCGACTC T TGTAGAATG     180

AACTAGGTAC AATAGAAGTA AAAACATGG CCAAAATTTG CGGCATCCTT T TGCAATGCA      240

ACCAAACGCT TTGTAGTTTG CAACATTGTT GAAGTCATTG AAGATCATTC A GGAGTACGC    300

ATAGCTCTGG CCCACCTAGC TGTCAAGCCT AGGGTAGCGA AAAACAGGTG T TAGGTAAGA    360

GTATTCGTTA CTAAGGTGTT GTTTGGTTCA ACCACAAAAG AGGCAACACT A ATTAGGAAT    420

AGCTGCTCCT GGTATCTGTT ATGATGCAAT GATCATCGGT TTTTGTTTGG T TGCAACCAA    480

TGTGAGCAGT GAAATAGCGT GGCATTGAAT CATAGCTAGA TGGGAGCATT A ATGATTTTT    540

CACAAGCCTG TATCAGATGT CACTGTGATC GATTGCAGCC TATTGCAACC A AATTTAAAG   600

TTATGATAAC AGATACCGAT GTAAACTAAT CACTTCCCTA AATCGTCAAA C CAAACATTA   660

CATAAAGTTG ATAGGATCAA TGTAATTAAA AAGTACATGT CACGGAATAT T TATAGAGGG   720

CTCACCTTAT TCCATATACA AAGTCAAAAA TACCACTTAA CTTTTTTTAC A ATTATTCAT   780

TTATATAAGG ATAATCCGGT AATTTTATCT TACATATATA TTCCATACTT C TTTTGGGCA  840

CACAATCTTC ATCAGAGGCT TTGCTTCCTG TGAAGTGAAC CAATCTATCT T CTTTCGCTT  900

CTAACTTTGT TTCACGCCTC GCAAAGTGAA CCGATTTGCC TCCGTTCATT T CTGACTTCA  960

CTTCACATTC TACAAAGTGA ACGAGTCTGT CTCCATTTAC TTCTAACTTA G CTTTACTTT  1020

CTGCAAAGTG AACCGATCTT TCGTCGTTCA CTTTTGGTTT TACTTCATGT T CTATAAAGT  1080

GCACTAATGC GTCTTTGTTC ACTTCTTGCT TGCTTCTAAT GAAGATGATC C TAAAAATAA 1140

ATATCAAATA AATACAAAAA TAGTTGTTAA TCAACTTTCG AAACGTAAGG G ATTGCATTT 1200

GTCCGAGGCC AAATCCCTAA CAACAACCCC TAGTGGGCAA AAGCCTCCTC T GAAGGTACG 1260

AATCCTTTGA AATTATGATT TGGACCAGAG GTAAAATGTT ATCCTCAAGC T TCAGAGTTG 1320

TCTATTGGAG GTTAGGAGGT GAGTAGTTTC GATTTCAAAT TTGTAATGAC C AAGTTTCAA 1380

CAAAGTCAGG TATATAAGGA AGTTGAAGGG TCACTTTTGA CCAAAGCCAT G TATACATAC 1440

CGTGCTTTCT GGGTCATAGT TTGCTACTGC TTTGATGAAA ACAAGAGGTA T TGTTGCATG 1500

TTTTTATGAA TAAAAGCTTT TATGTGAAGT CTGTTTGTAG ATGTGTGTAT A AGCCTTGCA 1560

AGGAAGTTAT CCGCTTGTTG ATTGTGAAGC TTATGAAAGT AATTCCCAAC T GATAACTTG 1620

GTTTTTTTGT TTGTTGTATT ATGGTTTGGT TGACTCCTTT TTGTGTTGGA T GTTTAGTGT 1680

TGAATGGAAT CCCCATGTGT CTTCTTATGA TTTTGAGGAT GATTTAGAAG A TTTGGAAGT 1740

CTCTAGGTTA AAACTTGTTG ATGATGAAAC CAAGTCATTG AGGTTTGGAA A GTACTTGCT 1800

GGATGAAGCA ACTCTTAATT TTGTTTAGAG AAAAAATATT AACCAGGGAA T GAAACAGTC 1860

CTAAAGTCTA AAGTAGATGA ATGTGTTGTC TTTAAATACT TCATTACTAC C AGGCTCCAC 1920

TTTCCTTCCT TAGGATTTGT TGGGTTAGAT TGTAAGTTCA TACAACATCG G AGTGTATCA 1980

TTTGATGTCT AATGGTATTT CAAAGATTGC ACTTTTTGTT TCAGCCATCA A AACTCAAGA 2040
```

```
ATTAACTCTC AATGTAGTTG CATTTTGTTC TTTGAATGAG ATGCACTACC A ATTTAGAAG    2100

CTATAATAAA ATAGACCATA AACCTTAAAC CCCCCAAACC CAAAGCCCTA A ACCTTGGCC    2160

CCTACTCGGG CGCCGGCTAA TCAGTCATAC ACATCGATTT ACCGGCTTTG G GGAGTGGCT    2220

AATCGGTAAT CCTGGCAGAT ATATCATTTT ATTTCTTTTT TTTGTATTTT T TTAAACTTC    2280

CATATTTTTA GTTTGAAATC CGTTGCGTAT TTTGAAATTT GGTTTCAGCA G AAAGTCTTC    2340

AAATAATCCA TAGTATTTAT ACAAAAATTG GCATCAAAAG TTTTTAGAAT T TACAAAATT    2400

CAAATTCAAA ACCGGTGATA CGGTGGAGCC GTCCGCCATC GATAACAGGC T AGCCGGATT    2460

TATCAATCGG CTTCGTGACC ATTGATCGGA GCTCGCTCGC ATGCAGGAAG T AAATACAAT    2520

GCATGGATCA CAAACTAAAC TATGTGCCAA GACTCAACAT GTGTAACATC A TTCTTGTTG    2580

AGCATATGAT AATTTACTTG TCATAACAAA ATAAAGAATA GAGCAAAATC C ACTTTGGTC    2640

CTCTTTGGCA TGGCTCTTTA GGCGGCTCCA GCTCAGACTC ATTATGAAGC C CTATCAAAT    2700

AGTAAAAAAA CGGCTCCTTG TCCAGAGCCC TCCAAGAGCT ATAGCCGTTT T ATTGTTGGG    2760

ACCCAAAGCA CAAAAAACGT AGCTTCTACT GGCTCCTACA TTTTTCTCAT A CGTCATTCC    2820

AAAAGAAATA CATAATAAGT TGTTTTGCCA AACAAATTGC AAAATGGCTC C GGCTCCGCT    2880

AGAGAAGCTA AGGAGATAAA AGAAACAGAG CCGAAACTGT TTTCAGAGGA G CCAGAGCCC    2940

TGCTAAGGGC TTGTTCGGTT ATACCAATCC AGAAGGGGAT TGGAGGAGAT T AAATGACTA    3000

GGAGGGGATT TAATCCCCTC CAATCTCCTT CTGAATTGGT ATAACCGAAC A TGCCCTAAA    3060

GGAGGCCTTT GTATGCTTCA TCTTAGAGAG GAATCGAATA AAAGTCGTGT G CTACTTGTT    3120

TTCGCCGTTA ATTCCTCGTG GCTAGCTTGT GCCATTGCAT CCATTGATCC A TAGTGGTGG    3180

TAAATTAACA TGCTACATCT TTTATTGTGT CATCCTGTGG TCACCAGTGG T CTGAGAGAA    3240

GTGGAATTTA TTGTGCCAGC ATAGTTAAAA GACCTGTTAT TCGACTACAC T AGCAATATG    3300

TACTACTGTA GGGGTACTAT ATTTCACATA AGTAGGCAGT CTAATTCTAG C TCTTATTCT    3360

AAACGTCATT GAATTCACTG CTGAGGGAGC GATGGGCAAC AATGAATTGT C ATGCTCGCT    3420

TTCAACAACA CATGTAGCTC CTCTGGTAGT AGATTACGAG AGTGTTTGGT T TATAGAGAC    3480

TAATTTTTAA TTTATCTATT TTATTTTAAT AATTTAGAGA CTAAAATAGA A TAAAATGGA    3540

GGAACAAACC AAACACCCTT TAAATGCCCG ATCGGCTCCA ATTTTTTGGA T AGTAGTACT    3600

CCAGTAATAA CAGTTATGCT GGGTGCCTGG GTTGCCAACC GCTCATCAGT G CACTTATTT    3660

TTGGTATAGC CATGGAAGCT TGTACAGCTT GCAGCCATGC TTTCCCGGCT T CTCTATAAA    3720

ATGCAGGCAC TGCATTTCCA TATTCTCAAC GGCCCCAAGG GTCCACGTAG T CGAGGACTA    3780

CAGCAAGAAA TGGGGTCAA CAAGTCTGCA GTTCTGCTTG GTGTGGTTTT G GTCTCAGTC    3840

CTTCTCTTCC TGGACGTTGT GTACGCAAGG GAGCTCACTG AAGCCAATGG T TGCTAATCC    3900

GTCTCTCTCC CTGCTTTGTG TGTTCTGCAC TACTGTTAAC ATTAGTGCAT G AATTAACTA    3960

GAACCATTTT AAAGAAGGTA TATCTTTTTG TGCTTCATTC TTTCTTCATG C AGGCTCTGG    4020

AGTGAAGAAT AATGTGAAGC CTGCAGGAGA GCCTGGGCTC AAGGATGAGA A GTGGTTTGG    4080

TGGTGGATAC AAGCATGGTG GAGGGTATGG AAACAACCAG CCAGGATACG G TGGCGGAGG    4140

AAACAGCCAA CCTGGATACG GCGGCGGAGG AAACAGTCAG CCCGGATACG G TGGAGGATA    4200

CAAGCGCCAT CACCCTGGTG GCGGCTACGG GTCTGGACAA GGAGGGCCTG G ATGTGGATG    4260

TGGAGGAGGG TATGGAGGTG GCAATGGTAG TCCTGGGTAC GGCGATGACA A TGGTGGTGG    4320

CATTGGCACT GGTGGCGGAA ATGGCAATGC TGGTGGGTAC GGAGGAGGAG G CGGCGGTTA    4380

TGGAGGCGGC TACGGCAGTG GTAGTGGTAC AGCACCAGGA GGCGGATATC A TGGCGGTGG    4440
```

-continued

```
TGGTGCACAA CGCTACGCTG GGCAGAACTA GCAAGAACAA CCCCTTATGC T AGTTTATGT   4500

TAAATAAACG ATCCATTGTT CATGTGACTG AGCAATTTAA GCAGTGAAGG A TCTTGACTC   4560

GTGTTATTTG TGTTACCATA TGTATTGATT GTTTTATGTT TAAGATGAAT G TACACCGCT   4620

ATTTGTATGT CGAACTCGTT GCATGGAGAT GAAAAAAAAA GGCACAAAAA C ATCAGCAAA   4680

CCATGCTTTC CTTCCGGTCG ACCAGATTTG GGCTGATATT TATTGAGTAA A AAAAATTCT   4740

ATCTCTGGGA GATTGTTTCA GTAAAAGCT AGAGCGTGAC ATTTTGTAGC G GAAAATTGG    4800

AACGAAAACA TGTCCAACGT CGAAATTATT GTATATATTC TAATGGATAT A TATAACGTA   4860

ATCAGAAGGA AAATTGTTTC CAAGTCATTT TTTCACAATG CAACAGTCAA A CATGGATGC   4920

GGCGAGCGAA GGATGCAGGT GGGTTCCCCT GCCGCTCCAA ATCCTATAGA G CCCTCCTAA   4980

AGACTCCCCT AAAATTAGAT CTTATGTTTC TCATTATGTG TTTTAAGATT T TCATTATTC   5040

ATGGATGTTT CGATATAAGA CTATTTTGAA TTATCATATT TGTCTATTGT G AGTCGTTTA   5100

GGCCCCGTTT GGTTCTATTA GTCTTAGGAT GTGTCACACC CGGATTTAAG G GACAAATAA   5160

GCAAGGGTGA ACTTTTACAA TGTTAGAGTG TATAGAGATA AATGTCATAA T AATATTAGA   5220

GTACTTTTAC AATGCGGAAG TCTTACAAAA TAAAAGATAA ACATAAAATG A ACTAAAATC   5280

CATCTTTGGC GCCAATAAGT CAACTGAAAG ACGCCATCTA AATCAGATCG A ACTCCTCGT   5340

TGTGTGGCTC CTCTTGAACC ACCGGTCCTT CTCCTGTGGG GGGTGTGAGA C AGCAAGGGT   5400

GAGCTCACAC ATGATCATAG CTCAACAAGT TGTGGAGAAA CCAGTGAGCA T GAATTCAAC   5460

AATGGTGGGA GCTCATGTTA TGTGTAAGGC TGATAAACAA TAAGGGTTAA A GCTGAACAT   5520

TGCTTTTAAT AAGTTGGTCA AAATTTTATT AGTAGTTACT AAATGTAAGT G CATACCAAA   5580

CCATAATAGA AATAATAGAA CAAAATTAAT AAATGATCTC ATACAATGCA A ATGACAAAT   5640

TGAGTTTAAG TTCCATAATT TAATCCTGCG AGAGTCCTGA GTTGCTCATG A CCGTGAGCT   5700

CGGCTAGTAT ACCAGTTTTA CACTCTGCAG AGGTTGTACC CTGTACCCAT A AGTCATGTT   5760

ACCCATCTGC CAAGGGATCG CGACTCCCAT ACACCTCTAC CAAGGAAGCG A GGCAGGGCA   5820

ATACTACGAG GCCTTTACAA AGTTCCACTA GCTTCCGAAA ACCCGCTACA G TTTATGGGA   5880

AGAGCACTTA CAAGAATCCC CCGTCTGATC GCAATTGCAG CAAAATCAAC C CGAAAACCT   5940

CCTTGCATGC AACTCCCCTA CTGCCCTTGC CCCTTTCGGG TAAGGTAGTC T TCCACTAGC   6000

TTTCCTAATT AGTTAGCCAA GGGGTCTCAT TCCTCCCTTA TGGTGGCACG T GTTTCTCAA   6060

GTTAAGCTCC ATGTTCCAAT TAACATTAAT GATGTTGACA TGAACATAAA T AAAATAACA   6120

AATAATTGGA ACATGGATAT AATGATATAT TAACCCAAAA CCATGTGAAG C AATAGCAAA   6180

ACTACCCAAG TGATTCAGGG GTAACAAGGT AAAGAGTTAA ACAGTCTAGG G TGACCTATT   6240

CGGTCCCATC AGAATTAAAC CTATGCATGA ATAAGTGATA TTAAAGAACA T TATTGGGTA   6300

TAAAAGTGGT CAAGGGCACA ACTTGCCTTC AATGAGCTCC TACTCAACAA C TTCTATCTG   6360

CTGGGCACCA GGATCCCCCG GGCTGCAGGA ATTCGATATC AAGCTTATCG A TACCGTCGA   6420

CCTCGAGGGG GGGCCCGGTA CCCAATTCGC CCTATAGTGA GTCGTATTAC A ATTCACTGG   6480

CCGTCGTTTT ACAACGTCGT GACTGGGAAA ACCCTGGCG TTACCCAACT T AATCGCCTT    6540

GCAGCACATC CCCCTTTCGC CAGCTGGCGT AATAGCGAAG AGGCCCGCAC C GATCG       6596
```

(2) INFORMATION FOR SEQ ID NO:12:

(i) SEQUENCE CHARACTERISTICS:
        (A) LENGTH: 32 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "primer for B200i"

(iii) HYPOTHETICAL: NO (xi) SEQUENCE DESCRIPTION: SEQ ID NO:12:

AAAACTGCAG GAATTCACTG CTGAGGGAGC GA                                32

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer for B200i"

(iii) HYPOTHETICAL: NO (xi) SEQUENCE DESCRIPTION: SEQ ID NO:13:

GCGGGATCCT TCTTGCTGTA GTCCTCGACC ACG                               33

(2) INFORMATION FOR SEQ ID NO:14:

(i) SEQUENCE CHARACTERISTICS:
        (A) LENGTH: 1093 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: misc_ feature
        (B) LOCATION: 1090..1092
        (C) IDENTIFICATION METHOD : experimental
        (D) OTHER INFORMATION: /function= "ATG translation start"
            /evidence= EXPERIMENTAL (ix) FEATURE:
        (A) NAME/KEY: promoter
        (B) LOCATION: 1..1093
        (C) IDENTIFICATION METHOD : experimental
        (D) OTHER INFORMATION: /function= "5' Regulatory Region of
            P19"
            /evidence= EXPERIMENTAL (xi) SEQUENCE DESCRIPTION: SEQ ID NO:14:

CTCGAGGATC AATTTAAAAT GAAAACGGAA AAAGTGTAAA AGCTGGTCCA G AAAAATAAG    60

GTCCGAAGCT TCCAAAAACC GGGACGAGCG CCTCCCACGA AAGTGCATTA C GTGGGCCGG   120

CAAAACTACC CTAGCAAAGA ATGACCTGAA CCTAAGCGAT GTCTCAAATC T CGATGCCAC   180

GAGCAATCAA GGCGATGCCT TCAGAAGGAA ACAACGCCG TGACACACAA G CTTTGCATA   240

TTCATGAGAG AAGACCAAAA TAACAGTACG TGCCTCATTG CTTATTTTGT T TCCTCATAT   300

AACAGTACGT GCAGTTCAAC CCAGGTGTAT ATGTGTATCC CGCCACTTCT A TCGTTAGGA   360

AAGACTATAA ATACATCCAT TCATCTACGT ATCTCTCACG CTCTTTACTT T TGGCTTGCA   420

ATAATAATAC GACCAAAGAG ACTAGCGCAC CACAATACTA CATATACCCA T GCTGATAAT   480

CATACACCCG TCAATTCTAG CTGTGTCCAG GTCGAAGTAA CAGACGGGAA C ATCACGGTG   540

GTGATGCAAG AGACTAGCGC GTTTGGACGC TTCGCATCAC CTACCTTTGG A TGCCTCGCA   600
```

-continued

```
TGAATCAAGT CGTGTCGTCC GCTAGCTTCC GCCTACCACC CACGGAGCAG A GCCAGCGAG    660

CAACTAACAC CGGCCAACTA TCCACTGGAG TTGAATGCAG GACGTCCAAG G TGTGCCCGT    720

CAACCATTCT GCTGACCGTA GTCATGGCGA GCTGGTGCAG TTCAGTGCAT G CTCTAGGTC    780

TAGGGTAGAG TGTTCAACGG ATTGTTACAG CGGCCGTGGG CGATTCATTA G ACGGCTCCC    840

CGCAGGTGGG GTGTTCATTA TCCCCTGCAT CTTTCTTTAA TCGCTCACCT G CTCGGTCGG    900

CGGCGATGGC CGCGTACGCT CCCTACGTGT CGCCGCATGG CATGCACATG G CCGGCTCGG    960

GCCACGGCGG TGCGTGGCCA GCTATAAATA CCCCAGCCGG GAGCTCCTAG A TCCATCTCC   1020

ACACAACTAC CAGTACACTC CACTCCCATC ACACACACGG ACACACCTGC A AGAGCGAGA   1080

GCGTGAGCCA TGG                                                      1093
```